United States Patent [19]

Peterson et al.

[11] Patent Number: 5,804,569
[45] Date of Patent: Sep. 8, 1998

[54] EXOCYLIC-PHOSPHOETHANOLAMINES

[75] Inventors: Andrew C. Peterson; Haridasan K. Nair, both of Madison, Wis.

[73] Assignee: Clarion Pharmaceuticals Inc., Madison, Wis.

[21] Appl. No.: 818,378

[22] Filed: Mar. 14, 1997

[51] Int. Cl.$^6$ .................................................. A61K 31/685
[52] U.S. Cl. .................................................................. 514/77
[58] Field of Search ................................................... 514/77

[56] References Cited

U.S. PATENT DOCUMENTS 5,661,138  8/1997  Peterson et al. ............................ 514/77

FOREIGN PATENT DOCUMENTS 6917-4H  5/1990  Japan .

OTHER PUBLICATIONS

Acker, R.–D. *Tetrahedron Lett.* (1977) 39: 3407–3410.
Akin, A.C. and Harmon, K.M., *J. Mol. Struct.* (1994) 319: 55–64.
Ashby, E. C.; Boone, J. R. *J. Org. Chem.* (1976) 41: 2890–2895.
Bates, R. B.; Siahaan, T. J. *J. Org. Chem.* (1986) 51(9): 1432–1434.
Bell, G.D. et al., *Br. J. Pharmacol.* (1984) 81(1): 183–187.
Bhaderi, S.; Sharma, K.; Mukesh, D. *J. Chem. Soc. Dalton Trans.* (1993) 8: 1191–1200.
Billimoria et al. *Chem. Phys. Lipids* (1974) 12:327–343.
Bird, P.R. *J. Chem. Soc.* (1967) 447.
Boudjebel, H.; Goncalves, H.; Mathis, F. *Bull. Soc. Chim. Fr.* (1975) 5:628–634.
Bowman, R. S.; Stevens, D. R.; Baldwin, W. E. *J. Am. Chem. Soc.* (1957) 79: 87–92.
Braude, E. A.; Forbes, W. F.; Evans, E. A. *J Chem Soc (C)* (1953) 2202–2206.
Brault, J–F. and Chabrier, P., *Bull. Soc. Chim. Fr* (1974) 677–680.
Briggs, T.I.; Dutton, G. S. S.; Merler, E. *Can. J. Chem.* (1956) 34: 851–854.
Bromm, B. et al. *J. Neuroscience Lett.* (1995) 187(3): 157–160.
Brown, H. C.; Midland, M. M.; Kabalka, G. W. *Tetrahedron* (1986) 42(20): 5523–5530.
Brown, H. C.; Jadhav, P. K.; Mandal, A. K. *J. Org. Chem.* (1982) 47(26): 5074–5083.
Brown, H.C.; Liotta, D.; Breber, L. *J. Am. Chem. Soc.* (1977) 99: 3427–3431.
Brown, H.C.; Lynch, G. J.; Hammar, W. J.; Liu, L. C. *J. Org. Chem.* (1979) 44(12): 1910–1915.
Cannone, P.; Belanger, D.; Lemay, G. *Tetrahedron Lett.* (1981) 22: 4995.
Cheng, H–M.; Casida, J. E. *J. Agric. Food. Chem.* (1973) 21: 1037–1041.
Cope, A.C.; Hecht, J.K. *J. Am. Chem. Soc.* (1962) 84: 4872–4876.
Cope, A. C.; Moon, S.; Park, C. H. *J. Am. Chem. Soc.* (1963) 84(24): 4843–4849.
Coulthard, C. E.; Marshall, J.; Pyman, F. L. *J. Chem. Soc.* (1930) 280–291.
Decombe, J. *Bull. Soc. Chim. Fr.* (1945) 5(12): 651–657.
Downes, A. M.; Gill, N. S.; Lions, F. *J. Am. Chem. Soc.* (1950) 72: 3464–3467.
Eccles, R., *Journal of Pharmacy and Pharmacology* (1994) 46(8): 618–30.
Eibl, H. *Proc. Natl. Acad. Sci. USA* (1978) 75(9): 4074–4077.
Eliel, E. L.; Biros, F. J. *J. Am. Chem. Soc.* (1966) 88: 3334–3343.
Felkin, H.; Gault, Y.; Roussi, G. *Tetrahedron* (1970) 26: 3761–3778.
Grant, M. S.; Hickenbottom, W. J. *J. Chem. Soc.* (1959) 2513–2516.
Hennion, G. F.; Quinn, F. X. *J. Org. Chem.* (1970) 35: 3054–3058.
Hong, C.–Z. and Sherlock, F.G., *Am. J. Phys. Med. Rehabil.* (1991) 70: 29–33.
Jadhav, P. K.; Brown, H. C. *J. Org. Chem.* (1981) 46(14): 2988–2990.
Kitahonoki, K. *Chem. Pharm. Bull.* (1959) 7: 114–118.
Krapcho, A.P.; M.J. Maresch and J. Lunn *Synth. Commun.* (1993) 23(17):2443–2449.
Landa, S.; Macak, J. *Collect. Czech. Chem. Commun.* (1958) 23: 1322–1325.
Laude, E.A. et al., *Pulmonary Pharmacology* (1994) 7(3): 179–184.
Letsinger, R. L.; Traynham, J. G.; Bobko, E. *J. Am. Chem. Soc.* (1952) 74: 399–401.
Magolda, R.L.; Ripka, W.C.; Galbraith, W.; Johnson, P.R.; Rudnick; M.S. in "Prostaglandins, Leukotrienes, and Lipoxins," Bailey, J. M. ed.; New York: Plenum (1985); pp. 669–676.
Magolda, R.L. and Johnson, P.R. *Tetrahedron Lett.* (1985) 26(9): 1167–1170.
Martin, S.F.; Wong, Y.–L; Wagman, A.S. *J. Org. Chem.* (1994) 59(17): 4821–4831.

(List continued on next page.)

*Primary Examiner*—Raymond Henley, III
*Attorney, Agent, or Firm*—DeWitt Ross & Stevens S.C.; Salvatore R. Conte, Esq.

[57] ABSTRACT

Disclosed are the use of certain cycloalkyl- and aryl-phosphoethanolamines as anti-inflammatory, anti-arrhythmic and local anesthetic agents. These therapeutically active cycloalkyl- and aryl-phosphoethanolamines are of the general Formula I:

$$R\text{—}O\text{—}PEA \qquad \qquad I$$

wherein R is an unsubstituted or a substituted $C_{5-7}$ cycloalkyl or an unsubstituted or a substituted phenyl in which each substituent is hydrogen or an unsubstituted or substituted straight or branched $C_{1-4}$ alkyl or $C_{2-4}$ alkenyl, said substitution being one or more of $C_{1-4}$ alkoxy, halo or cyano; and —O—PEA represents a phosphoethanolamine substituent. Also disclosed are intermediates for producing Formula I compounds.

35 Claims, 2 Drawing Sheets

OTHER PUBLICATIONS

Martin, S.F. and A. S. Wegman *J. Org. Chem.* (1993) 58: 5897–5899.

Merckx, E. M.; Lepoivre, J. A.; Lemiere, G. L.; Alderweireldt, F. C. *Org. Magn. Reson.* (1983) 21(6): 380–387.

Miciak, A. et al., *Biochemical Pharmacology* (1986) 35(20): 3489–3494.

Miller et al., *J. Org. Chem.* (1978) 43(17): 3384–3388.

Mironov, V. A. *J Gen. Chem. USSR (Engl. Trans.)* (1962) 32(8): 2688–2694.

Mironov, V. A. *J. Gen. Chem. USSR (Engl Trans.)* (1962) 32(8): 2680–2687.

Miyamoto, N.; Isiyama, S.; Utimoto, K.; Nozaki, H. *Tetrahedron* (1973) 29: 2365–2371.

Moleyar, V. and Narasimham, P., *International Journal of Food Microbiology* (1992) 16(4): 337–342.

Morgan, G. T.; Pettet, A. E. *J. Chem. Soc.* (1934) 418–420.

Muraro, G.; Cagniant, D.; Gagniant, P. *Bull. Soc. Chim. Fr.* (1973) 5(1): 343–350.

Nolen, H.W. et al., *Pharmaceutical Research* (1994) 11(12): 1707–1711.

Orr, G.A.; Brewer, C.F.; Heney, G. *Biochemistry* (1982) 21: 3202–3206 "Pharmacological Methods in the Control of Inflammation," Joseph Y. Chang and Alan J. Lewis (eds), Alan R. Liss, Inc. New York, pp. 221–223 (1989).

Papa et al., *J. Org. Chem.* (1942) 7: 587–589.

Pianka, M.; Edwards, J. D. *J. Chem. Soc. (C)* (1967) 2281–90.

Read, R. R.; Mullen, D. B. *J. Am. Chem. Soc.* (1928) 50:1763–1765.

Saari, W.S.; J.E. Schwering; P.A. Lyle; S.J. Smith and E.L. Englehardt *J. Med. Chem.* (1990) 33:97–101.

Saddler, J. C.; Conrad, P. C.; Fuchs, P. L. *Tetrahedron Lett.* (1978) 5079–5082.

Sarma, R. et al., *J. Am. Chem. Soc.* (1978) 100(14): 4453–4457.

Sehgal, R. K.; Koenigsberger, R. U.; Howard, T. J. *J. Org. Chem.* (1975) 40: 3073–3078.

Taniguchi, Y. et al., *Nippon Yakurigaku Zusshi–Folia Phannacologica Japonica* (1994) 104(6): 433–46.

Thuong, N.T. and Chabrier, P. *Bull. Soc. Chim. Fr.* (1974) 667–671.

Vasilenko, I.; De Kruijff, B.; Verkleij, A. J. *Biochim. Bioshys. Acta* (1982) 685: 144–152.

Zanker, K.S. et al. *Respiration* (1980) 39(3):150–157.

EXOCYLIC-PHOSPHOETHANOLAMINES

The present invention is directed to the use of certain exocyclic-phosphoethanolamines as anti-inflammatory, anti-arrhythmia, and local anesthesic agents, and pharmaceutical compositions containing such compounds. The invention also embraces certain novel intermediates used in making the compounds, as well as novel exocyclic-phosphoethanolamines.

DESCRIPTION OF THE PRIOR ART

All of the references cited below are incorporated herein by reference in their entireties.

Menthol and related compounds have a variety of biological activities. A review of the pharmacology of menthol is available: Eccles, R. *Journal of Pharmacy and Pharmacology* (1994) 46(8): 618–30. The local anesthetic properties of L-menthol for relief of dermal pain have been reported in Hong, C.-Z. and Shellock, F. G. *Am. J. Phys. Med. Rehabil.* (1991) 70: 29–33. In addition, menthol has also been shown to reduce the itch sensation (pruritis): Bromm, B. et al. *J. Neuroscience Lett.* (1995) 187(3): 157–160. A variety of effects which contribute to the pulmonary activity of menthol have been described. Menthol is indicated for the treatment of upper respiratory tract infections: Laude, E. A. et al. *Pulmonary Pharmacology* (1994) 7(3): 179–184. The ability of menthol to act as a pulmonary surfactant is described: Zanker, K. S. et al. *Respiration* (1980) 39(3):150–157. Furthermore, menthol has been shown to possess anti-bacterial activity against food borne *Staphylococcus sp., Micrococcus sp.; Bacillus sp.* and *Enterobacter sp.*: Moleyar, V. and Narasimham, P. *International Journal of Food Microbiology* (1992) 16(4): 337–342. These attributes of menthol contribute to its weak efficacy in pulmonary diseases. Few examples of menthol or related alcohols or phenols with anti-inflammatory activity have been reported. The menthol conjugate, menthol-β-D-glucuronide, has been described as a prodrug which is active against irritable bowel syndrome: Nolen, H. W. et al. *Pharmaceutical Research* (1994) 11(12): 1707–1711. However, in the abstract of Taniguchi, Y. et al. *Nippon Yakurigaku Zasshi-Folia Pharmacologica Japonica* (1994) 104(6): 433–46, it is described that L-menthol does not inhibit carrageenin-induced paw edema of rats nor the synthesis of prostaglandin E2 (an anti-inflammatory marker) in vitro. Cyclohexanols and methylcyclohexanols are reported to be inhibitors of hepatic HMGCoA reductase in vivo and to have choleretic and cholelitholytic activity: Bell, G. D. et al. *Br. J. Pharmacol.* (1984) 81(1): 183–187 and Miciak, A. et al. *Biochemical Pharmacology* (1986) 35(20): 3489–3494.

The synthesis of several alkylphosphocholines and arylphosphocholines have been reported in the literature. The synthesis of acyclic alkylphosphocholines for investigations into their Phospholipase $A_2$ inhibitory activity and their inhibition of the release of arachidonic acid (a precursor of inflammatory mediators) is described in Magolda, R. L. and Johnson, P. R. *Tetrahedron Lett.* (1985) 26(9): 1167–1170. The phospholipase $A_2$ inhibitory activity of these acyclic alkylphosphocholines are described in Magolda, R. L.; Ripka, W. C.; Galbraith, W.; Johnson, P. R.; Rudnick; M. S. in "Prostaglandins, Leukotrienes, and Lipoxins," Bailey, J. M. ed.; New York: Plenum (1985); p. 669–676. The synthesis of cyclopentylphosphocholine is described in Sarma, R. et al. *J. Am. Chem. Soc.* (1978) 100(14): 4453–4457. The synthesis of phenylphosphocholine (also known as phenyl choline phosphate) is described in Bird, P. R. *J. Chem. Soc.* (1967) 447, Brault, J-F. and Chabrier, P. *Bull. Soc. Chim. Fr* (1974) 677–680 and Akin, A. C. and Harmon, K. M. *J. Mol. Struct.* (1994) 319: 55–64. The syntheses of L-menthylphosphocholine and thymylphosphocholine are described in Thuong, N. T. and Chabrier, P. *Bull. Soc. Chim. Fr.* (1974) 667–671. A general disclosure of water soluble phosphocholine derivatives of compounds which are medically or pharmaceutically active is described in Honda, T. *JP Patent* 6917-4H (17 May, 1990). The synthesis of a variety of simple alkyl-, cycloalkyl- and aryl-phosphocholines have been described.

The prior art does not disclose or suggest, however, the use of exocyclic phosphoethanolamines for the treatment of inflammation, arrhythmia, cough or local pain (e.g., muscle, skin, opthalmic, rectal, throat, and joint pain).

DESCRIPTION OF THE INVENTION

Figure 1:
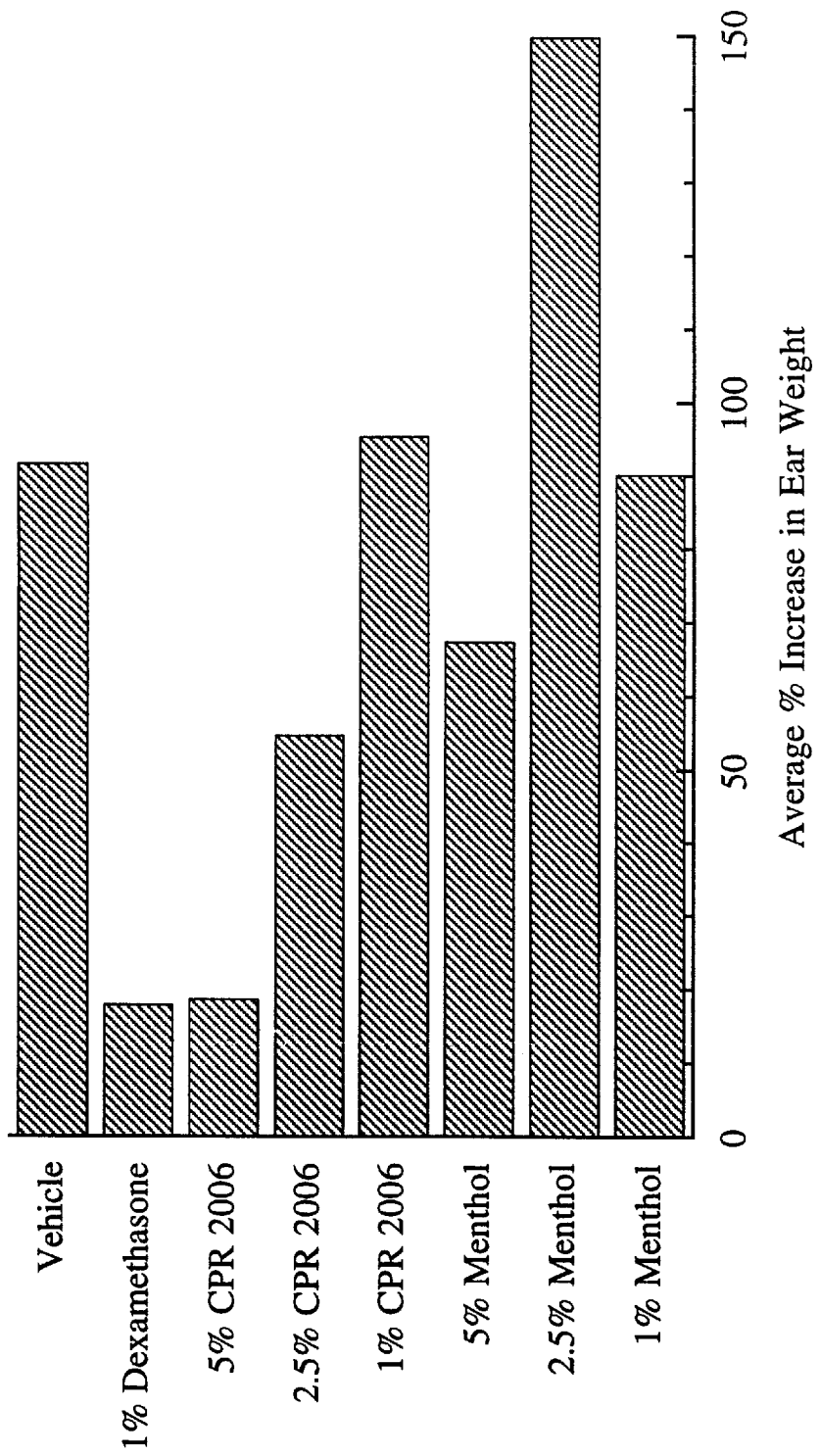
FIG. 1 is a graphical representation of results from an in vivo assay evaluating inhibition of phorbol myristate acetate (PMA)-induced inflammation in mouse ears by a representative compound of the invention, designated CPR-2006.

The exocyclic phosphoethanolamines having the anti-inflammatory, anti-arrhythmic and local anesthetic utilities of the instant invention are represented by the general formula:

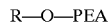

R—O—PEA        I wherein:

R is, preferably, an unsubstituted or a substituted $C_{5-7}$ cycloalkyl of the formula:

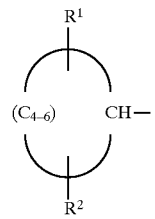

or an unsubstituted or a substituted phenyl of the formula:

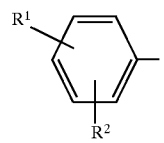

in which each $R^1$ and $R^2$ represents an unsubstituted or a substituted straight or branched $C_{1-4}$ alkyl or $C_{2-4}$ alkenyl, said substitution being one or more of $C_{1-4}$ alkoxy, halo or cyano; and OPEA represents a phosphoethanolamine moiety of the formula:

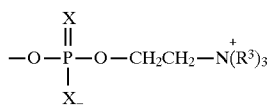

in which each R³ is independently hydrogen or methyl and each X is independently oxygen or sulfur.

When the X's are a combination of oxygen and sulfur, the —OPEA moiety can be written in two canonical forms:

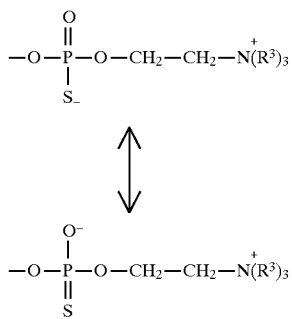

These canonical forms depict the same moiety; the true form being a hybrid of both canonical forms, as is known in the art.

When all of said R³ are hydrogen and X and Y are oxygen, the —OPEA moiety is known as a phosphoethanolamine moiety; when all three of said R³ are methyl and X and Y are oxygen, the —OPEA moiety is known as a phosphocholine moiety; with only one methyl and X and Y are oxygen, a phospho(N-methylethanolamine) moiety; and with two methyls and X and Y are oxygen, a phospho(N,N-dimethylethanolamine) moiety.

When all of said R³ are hydrogen and X and Y are sulfur, the —OPEA moiety is known as a dithiophosphoethanolamine moiety; when all three of said R³ are methyl and X and Y are sulfur, the —OPEA moiety is known as a dithiophosphocholine moiety; with only one methyl and X and Y are sulfur, a dithiophospho(N-methylethanolamine) moiety; and with two methyls and X and Y are sulfur, a dithiophospho(N,N-dimethylethanolamine) moiety.

When all of said R³ are hydrogen and X and Y are a combination of oxygen and sulfur, the —OPEA moiety is known as a thiophosphoethanolamine moiety; when all three of said R³ are methyl and X and Y are a combination of oxygen and sulfur, the —OPEA moiety is known as a thiophosphocholine moiety; with only one methyl and X and Y are a combination of oxygen and sulfur, a thiophospho(N-methylethanolamine) moiety; and with two methyls and X and Y are a combination of oxygen and sulfur, a thiophospho(N,N-dimethylethanolamine) moiety.

Within said Formula I, the cycloalkyls of Formula II and the phenyls of Formula III are preferred:

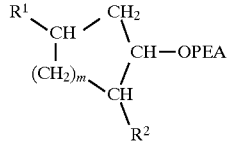 (II)

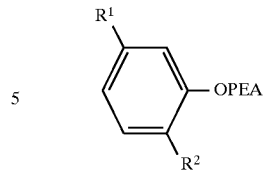 (III)

wherein m is the integer 1, 2 (preferred) or 3, and each of R¹, R² and OPEA is as previously defined. R¹ is preferably $C_{1-4}$ alkyl with methyl most preferred. R² is preferably $C_{1-4}$ alkyl or $C_{2-4}$ alkenyl with isopropyl most preferred. Both R¹ and R² can be substituted one or more times, preferably once, with substituents which do not interfere during the synthetic steps of making the subject compounds such as previously described, preferably halo, methyl or methoxy. The term "halo" represents fluoro, bromo, chloro and iodo, with fluoro and chloro being preferred.

The most preferred compound of Formula II is that denoted herein as CPR-2006, wherein R¹ is methyl, R² is isopropyl and OPEA is phosphocholine, namely, menthylphosphocholine, also chemically identified as L-menthylphosphocholine or (1R, 2S, 5R)-menthylphosphocholine.

Other particular compounds of Formula II are: menthylphospho(N-methylethanolamine), menthyl(N,N-dimethylphosphoethanolamine); menthylphosphoethanolamine; menthyldithiophosphocholine; menthyldithiophospho(N-methylethanolamine); menthyldithiophospho(N,N-dimethylethanolamine); menthyldithiophosphoethanolamine; menthylthiophosphocholine; menthylthiophospho(N-methylethanolamine); menthylthiophospho(N,N-dimethylethanolamine); menthylthiophosphoethanolamine; cyclohexylphosphocholine; cyclohexylphosphoethanolamine; cyclohexyldithiophosphocholine; cyclopentylethanolamine; (3-methylcyclohexyl)-thiophosphocholine; (2-methylcyclohexyl)-dithiophosphoethanolamine; (2-methylcyclohexyl)-dithiophospho(N-methylethanolamine); (2-isopropyl)-cyclohexylphosphocholine; isopulegylphosphocholine (also named as (5-methyl-2-(1-methylethylidene)cyclohexyl)-phosphocholine); (2-methyl-5-(2'-chloropropyl)cyclohexyl)-phosphocholine; (2-methyl-5-(2'-cyanopropyl)cyclohexyl)-phosphocholine; (2-methyl-5-(2'-methoxypropyl) cyclohexyl)-phosphocholine; (3-methoxymethyl-cyclohexyl)-phosphocholine; (2-methyl-4-(2'-chloropropyl) cyclopentyl)-phosphocholine; (3-chloromethyl-cyclopentyl)-phosphocholine; (2-methyl-5-(2'-cyanopropyl)cycloheptyl)-phosphocholine; (2-methyl-5-(2'-methoxypropyl) cyclohexyl)-phospho(N-methylethanolamine); (2-methyl-5-(2'-cyanopropyl)cyclohexyl)-phospho(N,N-dimethylethanolamine); (2-methyl-5-(2'-cyanopropyl) cyclohexyl)-phosphoethanolamine; (2-methyl-5-(2'-methoxypropyl)cyclohexyl)-thiophosphocholine; and (3-methoxymethyl-cyclohexyl)-dithiophosphocholine.

The most preferred compound of Formula III is that wherein R¹ is methyl, R² is isopropyl and OPEA is phosphocholine, namely thymylphosphocholine, also chemically identified as (5-methyl-2-isopropyl-1-phenyl)-phosphocholine.

Other particular compounds of Formula III are: thymylphospho(N-methylethanolamine); thymylphospho(N,N-dimethylethanolamine); thymylphosphoethanolamine; thymyldithiophosphocholine; thymyldithiophospho(N-methylethanolamine); thymyldithiophospho(N,N-dimethylethanolamine); thymyldithiophosphoethanolamine; thymylthiophosphocholine; thymylthiophospho(N- methylethanolamine); thymylthiophospho(N,N-dimethylethanolamine); thymylthiophosphoethanolamine; (2,5-dimethylphenyl)-phosphocholine; carvacrylphosphocholine (also named as (2-methyl-5-(1-methylethyl)phenyl)-phosphocholine); (2-tert-butyl-5-methylphenyl)-phosphocholine; (2-methyl-5-(2'-chloropropyl)phenyl)-phosphocholine; (2-methyl-5-(2'-cyanopropyl)phenyl)-phosphocholine; (2-methyl-5-(2'-methoxypropyl)phenyl)-phosphocholine; (3-methoxymethyl-phenyl)-phosphocholine; (3-methoxymethyl-phenyl)-phospho(N-methylethanolamine); (3-cyanomethyl-phenyl)-phospho(N,N-dimethylethanolamine); (3-chloromethyl-phenyl)-thiophosphocholine; (3-cyanomethyl-phenyl)-thiophospho(N-methylethanolamine); (2-methyl-5-(2'-methoxypropyl)phenyl)-dithiophosphocholine; (2-methyl-5-(2'-methoxypropyl)phenyl)-dithiophospho(N,N-dimethylethanolamine) and (3-chloromethyl-phenyl)-dithiophospho(N,N-dimethylethanolamine).

The compounds of Formula I may exist in isomeric form. For example, the compounds of Formula II may have an asymmetric carbon at the C-1 position of the cycloalkyl moiety and, consequently, they can exist in the form of different combinations of R and S isomeric forms as enantiomers, diastereomers or racemates. The compounds of Formula II may also have an asymmetric carbon at the C-2 and C-4 positions of the cyclopentyl moiety, or the C-2 and C-5 positions of the cyclohexyl moiety, or the C-2 and C-6 positions of the cycloheptyl moiety, and, consequently, they can exist in the form of different combinations of R and S isomeric forms as enantiomers, diastereomers or racemates. In addition, the compounds of Formula I may have an asymmetric carbon within $R^1$ or $R^2$ and, consequently, they may also exist in different R and S isomeric forms. Additionally, when X of the OPEA moiety is a combination of one oxygen and one sulfur atom, the phosphorus atom bonded to the X atoms has an asymmetric phosphorus atom and, consequently, may also exist in different R and S forms. Substantially pure forms of the isomers may be obtained by known resolution methodologies such as selective crystallization, column chromatography, starting the preparation from the optically pure isomer of an appropriate precursor (for example, the starting compound (A) shown in Reaction Scheme 1), or kinetic resolution.

In addition cis- and trans-geometric isomers may also be present in the subject compounds, e.g. when $R^1$ or $R^2$ in Formula II and Formula III is $C_2$–$C_4$ alkenyl, due to the cis- and trans-configuration inherent with the double bond. Thus, by initially starting with an appropriate cis- or trans-precursor, the corresponding end product of Formula I will be obtained.

All racemic and isomeric forms of the compounds of Formula I, including pure enantiomeric, diastereomeric and geometric isomers and mixtures thereof, are within the scope of this invention. Unless, otherwise specified, the compounds of the hereinafter examples are in racemic form.

The invention also comprehends salts of the Formula I compounds. Such salts include acid addition salts such as those made from inorganic acids such as hydrochloric, nitric, and the like acids or from organic acids such as citric, lactic and the like organic acids. The salts also include those made with bases such as sodium and potassium hydroxide. The salts of the invention are made by conventional methods well known to those skilled in the art. The salts for therapeutic use of the Formula I compounds are pharmaceutically-acceptable salts, as well understood in the art.

Another aspect of the instant invention is the novelty of certain Formula I compounds (including isomeric forms and salts thereof) and pharmaceutically-acceptable compositions comprising the same, as indicated hereinafter.

It has now been found that the Formula I compounds, including their pharmacologically active isomers and pharmaceutically-acceptable salts, possess anti-inflammatory, anti-arrhythmic and local anesthetic activities. Accordingly, they are useful, respectively, in the treatment of disease conditions wherein inflammation is a contributing factor, in the treatment of heart conditions to counteract fibrillation, and in the treatment of local pain.

Menthol and related compounds often have a particular odor. For instance, menthol has a distinctly identifiable odor and taste of peppermint; indeed, menthol is a major ingredient of peppermint extracts. Patient compliance is often compromised by treatment with odorous or distasteful medications. The phosphoethanolamines of Formula I do not have a noticeable odor. In addition, menthol and related cycloalkyl alcohols are poorly soluble in water, whereas the exocyclic phosphoethanolamines of Formula I are readily soluble in water. This enhanced water solubility improves the ease of formulation in aqueous solutions and other preparations. The phosphoethanolamines of Formula I also retain their lipid solubility properties. This amphoterism generally assists in the pharmaceutical formulation of the Formula I compounds. Since skin and tissues are comprised of phospholipids related to the Formula I compounds, the Formula I compounds are able to penetrate tissues and skin readily.

The invention thus provides a method of treating a host mammal afflicted with an inflammatory disorder comprising administering to said mammal an effective anti-inflammatory amount of a compound of Formula I or a pharmaceutically-acceptable salt thereof and a pharmaceutically-acceptable carrier. A further aspect of the invention provides a method of treating a host mammal afflicted with local pain comprising administering to said mammal an effective local anesthetic amount of a compound of Formula I or a pharmaceutically-acceptable salt thereof and a pharmaceutically-acceptable carrier. Another aspect of the invention provides a method of topical treatment of a host mammal with an effective local anesthetic or anti-inflammatory amount of an odorless, water soluble and dermal penetrating compound of Formula I or a pharmaceutically-acceptable salt thereof and a pharmaceutically-acceptable carrier. Still another aspect of the invention provides a method of treating a host mammal afflicted with an arrhythmic disorder comprising administering to said mammal an effective anti-arrhythmic amount of a compound of Formula I or a pharmaceutically-acceptable salt thereof and a pharmaceutically-acceptable carrier.

CHEMISTRY

The compounds of Formula I are either known or may be prepared by one or more of the synthetic procedures outlined in the following Reaction Schemes 1 through 5 and subsequent examples. Work up of the individual stepwise products in the synthetic procedures may be advantageously carried out if necessary by standard methodologies, for example, by evaporating the reaction solution or precipitating the particular product from the reaction solution by dilution with an appropriate antisolvent. The intermediate products obtained may be suitable for the preparation of the final products without further purification. Purification of either the intermediate or the final products is readily achieved by conventional methods such as recrystallization techniques, chromatography and the like.

REACTION SCHEME 1

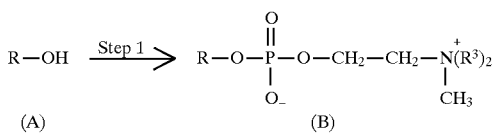

The compounds of formula (A) are commercially available or are known in the literature or are obtainable by art recognized procedures:

Cyclopentanol, trans-2-methylcyclopentanol, (+/−)-3-methylcyclopentanol, 2-methylcyclohexanol, (+/−)-cis-2-methylcyclohexanol, (+/−)-trans-2-methylcyclohexanol, 2-ethylcyclohexanol, 2-tert-butylcyclohexanol, 3-methylcyclohexanol, (+/−)menthol, (1R, 2S, 5R)-(−)-menthol (also known as L-menthol), (1S, 2R, 5S)-(+)-menthol, (1S, 2R, 5R)-(+)-isomenthol, (1S, 2S, 5R)-(+)-neomenthol, dihydrocarveol, isopulegol, cycloheptanol, phenol, ortho-cresol, 3-ethylphenol, 2-propylphenol, 2-isopropylphenol, 2-sec-butylphenol, 2-tert-butylphenol, 2-allylphenol, 2-propenylphenol, meta-cresol, 3-ethylphenol, 3-iso-propylphenol, 3-tert-butylphenol, 2,5-dimethylphenol, thymol (also known as 5-methyl-2-isopropyl-1-phenol), carvacrol (also known as 2-methyl-5-(1-methylethyl)phenol) and 2-tert-butyl-5-methylphenol are commercially available from Aldrich Chemical Company, Inc., 1001 West Saint Paul Avenue, Milwaukee, Wis. 53233 USA.

2-Alkylcyclopentanols are known in the literature or are obtainable by art-recognized procedures, for example: Cannone, P.; Belanger, D.; Lemay, G. *Tetrahedron Lett.* (1981) 22: 4995, Brown, H. C.; Midland, M. M.; Kabalka, G. W. *Tetrahedron* (1986) 42(20): 5523–5530, Hennion, G. F.; Quinn, F. X. *J. Org. Chem.* (1970) 35: 3054–3057, Brown, H. C.; Jadhav, P. K.; Mandal, A. K. *J. Org. Chem.* (1982) 47(26): 5074–5083, Jadhav, P. K.; Brown, H. C. *J. Org. Chem.* (1981) 46(14): 2988–2990, and Felkin, H.; Gault, Y.; Roussi, G. *Tetrahedron* (1970) 26: 3761–3778.

3-Alkylcyclopentanols are known in the literature or are obtainable by art-recognized procedures, for example: Merckx, E. M.; Lepoivre, J. A.; Lemiere, G. L.; Alderweireldt, F. C. *Org. Magn. Reson.* (1983) 21(6): 380–387, Brown, H. C.; Liotta, D.; Breber, L. *J. Am. Chem. Soc.* (1977) 99: 3427–3431, Bhaderi, S.; Sharma, K.; Mukesh, D. *J. Chem. Soc. Dalton Trans.* (1993) 8: 1191–1200, Brown, H. C.; Lynch, G. J.; Hammar, W. J.; Liu, L. C. *J. Org. Chem.* (1979) 44(12): 1910–1915 and Ashby, E. C.; Boone, J. R. *J. Org. Chem.* (1976) 41: 2890–2895.

2,4-Dialkylcyclopentanols are known in the literature or are obtainable by art-recognized procedures, for example: Mironov, V. A. *J. Gen. Chem. USSR (Engl Trans.)* (1962) 32(8): 2680–2687 and Mironov, V. A. *J. Gen. Chem. USSR (Engl. Trans.)* (1962) 32(8): 2688–2694.

2-Alkylcycloheptanols are known in the literature or are obtainable by art-recognized procedures, for example: Cope, A. C.; Hecht, J. K. *J. Am. Chem. Soc.* (1962) 84: 4872–4876, Miyamoto, N.; Isiyama, S.; Utimoto, K.; Nozaki, H. *Tetrahedron* (1973) 29: 2365–2371, Braude, E. A.; Forbes, W. F.; Evans, E. A. *J. Chem. Soc. (C)* (1953) 2202–2206, Saddler, J. C.; Conrad, P. C.; Fuchs, P. L. *Tetrahedron Lett.* (1978) 5079–5083 and Sehgal, R. K.; Koenigsberger, R. U.; Howard, T. J. *J. Org. Chem.* (1975) 40: 3073–3078.

3-Alkylcycloheptanols are known in the literature or are obtainable by art-recognized procedures, for example: Cope, A. C.; Moon, S.; Park, C. H. *J. Am. Chem. Soc.* (1963) 84(24): 4843–4849.

2,4-Dialkylcycloheptanols are known in the literature or are obtainable by art-recognized procedures, for example: Muraro, G.; Cagniant, D.; Gagniant, P. *Bull. Soc. Chim. Fr.* (1973) 5(1): 343–350.

2-Alkyl-cyclohexanols are known in the literature or are obtainable by art-recognized procedures, for example: Letsinger, R. L.; Traynham, J. G.; Bobko, E. *J. Am. Chem. Soc.* (1952) 74: 399, Acker, R.-D. *Tetrahedron Lett.* (1977) 39: 3407–3410; Miller et al. *J. Org. Chem.* (1978) 43(17): 3384–3388, and Papa et al. *J. Org. Chem.* (1942) 7: 587–589.

3-Alkyl-cyclohexanols are known in the literature or are obtainable by art-recognized procedures, for example: Eliel, E. L.; Biros, F. J. *J. Am. Chem. Soc.* (1966) 88: 3334–3336.

2,5-Dialkylcyclohexanols are known in the literature or are obtainable by art-recognized procedures, for example: Decombe, J. *Bull. Soc. Chim. Fr.* (1945) 5(12): 651–656.

2-Alkylphenols, 3-Alkylphenols and 2,3-Dialkylphenols are known in the literature or are obtainable by art-recognized procedures, for example: Briggs, T. I.; Dutton, G. S. S.; Merler, E. *Can. J. Chem.* (1956) 34: 851–854, Bates, R. B.; Siahaan, T. J. *J. Org. Chem.* (1986) 51(9): 1432–1434, Pianka, M.; Edwards, J. D. *J. Chem. Soc. (C)* (1967) 2281–90, Read, R. R.; Mullen, D. B. *J. Am. Chem. Soc.* (1928) 50: 1765, Downes, A. M.; Gill, N. S.; Lions, F. *J. Am. Chem. Soc.* (1950) 72: 3464–3466, Bowman, R. S.; Stevens, D. R.; Baldwin, W. E. *J. Am. Chem. Soc.* (1957) 79: 87–88, Cheng, H-M.; Casida, J. E. *J. Agric. Food. Chem.* (1973) 21: 1037–1041, Grant, M. S.; Hickenbottom, W. J. *J. Chem. Soc.* (1959) 2513–2515, Morgan, G. T.; Pettet, A. E. *J. Chem. Soc.* (1934) 418–420, Kitahonoki, K. *Chem. Pharm. Bull.* (1959) 7: 114–117, Coulthard, C. E.; Marshall, J.; Pyman, F. L. *J. Chem. Soc.* (1930) 280–291, and Landa, S.; Macak, J. *Collect. Czech. Chem. Commun.* (1958) 23: 1322–1325.

Step 1:

The indicated phosphoethanolamine moiety, where X is oxygen and at least one of $R^3$ is methyl, is produced by reaction of the hydroxyl in Compound (A) with 2-chloro-2-oxo-1,3,2-dioxaphospholane (also known as 2-chloro-1,3,2-dioxaphospholane-2-oxide, Aldrich Chemical Co. Cat. No. 37,795-3) and a trialkylamine, such as triethylamine, in an inert aprotic solvent, such as toluene (preferred), benzene, chloroform, diethyl ether, dioxane, tetrahydrofuran and the like followed by reaction with the appropriate amine to yield Compound (B) by literature methods which are known in the art, for example, Thuong, N. T. and Chabrier, P. *Bull. Soc. Chim. Fr.* (1974) 667–671.

REACTION SCHEME 2

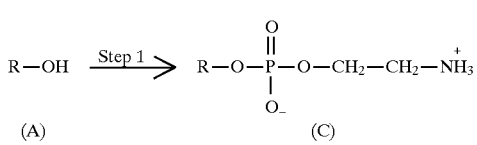

Step 1:

The indicated phosphoethanolamine moiety, where X is oxygen and all of $R^3$ are hydrogen, is produced by reaction of the hydroxyl in Compound (A) with phosphorus oxychloride and a trialkylamine, such as triethylamine, at low temperatures (0°–4° C.) in an anhydrous aprotic solvent, such as tetrahydrofuran (preferred), followed by reaction with ethanolamine and subsequent aqueous hydrolysis, to yield compounds of Formula (C) by literature methods known in the art, for example, Billimoria et al. *Chem. Phys. Lipids* (1974) 12:327, Eibl, H. *Proc. Natl. Acad. Sci. USA* (1978) 75(9): 4074–4077.

REACTION SCHEME 3

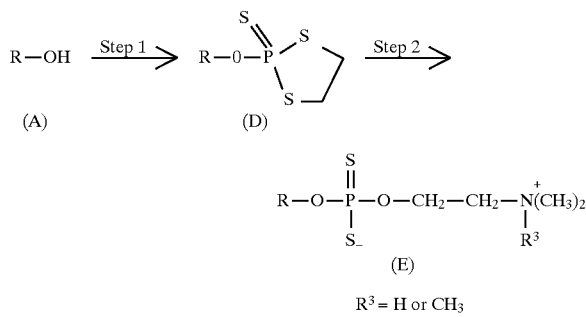

Step 1:

The dithiaphospholane moiety is produced by reaction of the hydroxyl in Compound (A) with 2-chloro-1,3,2-dithiaphospholane, which is prepared by procedures known in the literature (Boudjebel, H.; Goncalves, H.; Mathis, F. *Bull. Soc. Chim. Fr.* (1975) 5:628–634), at −38° C. in a dry oxygen-free aprotic solvent, such as, especially preferred tetrahydrofuran, followed by subsequent sulfuration with elemental sulfur in carbon disulfide to yield Compound (D) by the method of Martin, S. F.; Wong, Y.-L; Wagman, A. S. *J. Org. Chem.* (1994) 59(17): 4821–4831.

Step 2:

The dithiaphospholane moiety in Compound (D) is converted into the dithiophosphoethanolamine moiety in Compound (E) by treatment of Compound (D) with choline tosylate (commercially available from Sigma Chemical Co., St. Louis, Mo., Cat. No. C 5787) or N,N-dimethylaminoethanol (commercially available from Aldrich Chemical Co., Milwaukee, Wis.; Catalog No. D15,740-6) and 1,8-diazabicyclo(5.4.0)undec-7-ene (DBU; commercially available from Aldrich Chemical Co., Catalog No. 13,900-9) in acetonitrile at room temperature to yield Compound (E) by the method of Martin, S. F.; Wong, Y.-L; Wagman, A. S. *J. Org. Chem.* (1994) 59(17): 4821–4831.

The intermediate compounds of Formula (D) are believed to be novel and, accordingly, they constitute an additional aspect of this invention.

REACTION SCHEME 4

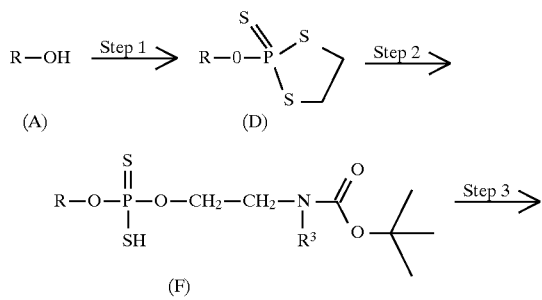

-continued
REACTION SCHEME 4

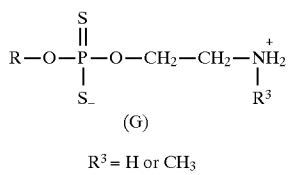

$R^3$ = H or $CH_3$

Step 1:

The dithiaphospholane moiety is produced by reaction of the hydroxyl in Compound (A) with 2-chloro-1,3,2-dithiaphospholane, which is prepared by procedures known in the literature (Boudjebel, H.; Goncalves, H.; Mathis, F. *Bull. Soc. Chim. Fr.* (1975) 5: 628–634), at −38° C. in a dry oxygen-free aprotic solvent, such as, especially preferred tetrahydrofuran, followed by subsequent sulfuration with elemental sulfur in carbon disulfide to yield Compound (D) by the method of Martin, S. F.; Wong, Y.-L; Wagman, A. S. *J. Org. Chem.* (1994) 59(17): 4821–4831.

Step 2:

The dithiaphospholane moiety in Compound (D) is converted into the dithiophosphoethanolamine moiety in Compound (F) by treatment of Compound (D) with N-(tert-butoxycarbonyl)ethanolamine (Aldrich Chemical Co. Catalog No. 38,202-7) or N-(tert-butoxycarbonyl-N-methyl)ethanolamine and DBU in dry acetonitrile at room temperature by the method of S. F. Martin and A. S. Wegman *J. Org. Chem.* (1993) 58: 5897–5899. N-(tert -Butoxycarbonyl-N-methyl)ethanolamine is prepared from N-methylethanolamine and di-tert-butyl dicarbonate (commercially available from Aldrich Chemical Co. Cat. No. 36,194-1) by the method of W. S. Saari; J. E. Schwering; P. A. Lyle; S. J. Smith and E. L. Englehardt *J. Med. Chem.* (1990) 33:97–101 or by the method of A. P. Krapcho; M. J. Maresch and J. Lunn *Synth. Commun.* (1993) 23(17):2443–2449.

Step 3:

The N-tert-butoxycarbonyl protected ethanolamine Compound (F) is converted into the dithiophosphoethanolamine Compound (G) by treatment of Compound (F) with excess 2.8M aqueous HF by the method of S. F. Martin and A. S. Wegman *J. Org. Chem.* (1993) 58: 5897–5899.

REACTION SCHEME 5

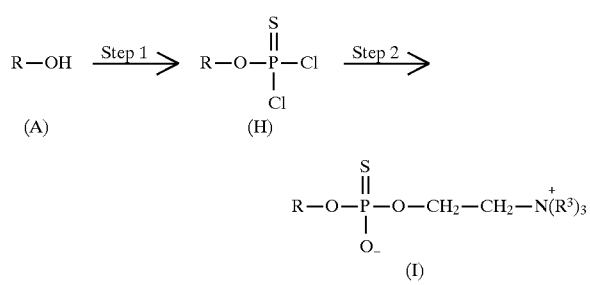

Step 1:

The thiophosphoryl dichloride moiety of Compound (H) is produced by reaction of the hydroxyl in Compound (A) with thiophosphoryl chloride, $PSCl_3$, (commercially available from Aldrich Chemical Co. Cat. No. 22,429-4) and an aprotic amine, such as pyridine (preferred) or triethylamine, in an inert aprotic solvent, such as trichloroethylene (preferred), toluene, benzene, chloroform, dichloromethane, diethyl ether, dioxane, tetrahydrofuran and the like to yield Compound (H) by literature methods known in the art, for example, Vasilenko, I.; De Kruijff, B.; Verkleij, A. J. *Biochim. Biophys. Acta* (1982) 685: 144–152 and Orr, G. A.; Brewer, C. F.; Heney, G. *Biochemistry* (1982) 21: 3202–3206.

Step2:

The thiophosphoryl dichloride moiety of Compound (H) is converted into the thiophosphoethanolamine moiety in Compound (I) by reaction of Compound (H) with the appropriate commercially available ethanolamine derivative (choline p-toluenesulfonate; N,N-dimethylethanolamine; N-methylethanolamine or ethanolamine) and an aprotic amine, such as pyridine (preferred) or triethylamine, in an inert aprotic solvent, such as tetrahydrofuran (preferred), trichloroethylene, toluene, benzene, chloroform, dichloromethane, diethyl ether, dioxane, and the like to yield compounds of Formula (I) by literature methods known in the art, for example, Vasilenko, I.; De Kruijff, B.; Verkleij, A. J. *Biochim. Biophys. Acta* (1982) 685: 144–152 and Orr, G. A.; Brewer, C. F.; Heney, G. *Biochemistry* (1982) 21: 3202–3206.

The intermediate compounds of Formula (H) are believed to be novel and, accordingly, they constitute a still further aspect of this invention.

A particular aspect of the subject invention is the novelty of certain compounds within Formula I as represented by the formula:

UTILITY

The compounds of Formula I, including the pharmaceutically-acceptable salts and isomeric forms thereof, are useful therapeutic agents for treating inflammation, arrhythmia and local pain. Among the mammals that may be treated with the subject compounds for the indicated utilities are, of course, humans.

I. ANTI-INFLAMMATORY

The anti-inflammatory activity of the herein-described compounds of Formula I and pharmaceutically-acceptable salts thereof may be assayed by methodologies conventional in the art, such as the following:

In Vivo Assay: Mouse Ear Inflammation Model

A common in vivo model for the evaluation of anti-inflammatory agents is phorbol myristate acetate (PMA)-induced inflammation in mouse ears. This method is described in "Pharmacological Methods in the Control of Inflammation," Joseph Y. Chang and Alan J. Lewis (eds), Alan R. Liss, Inc. New York, pp 221–223 (1989). In this assay, edema, which is characteristic of inflammation, is quantified by determining ear thickness or ear weight approximately 6 hours after applying PMA to the ear.

1. Mice: Male CD-1, 21–24 g (Product Number 3002) obtainable from Harlan Sprague Dawley, Indianapolis, Ind., USA.

2. Methodology:
   a. Prepare 0.01% (w/v) PMA in a mixture of equal volumes of acetone and ethanol and further containing 0 (vehicle), 1%, 2.5%, and 5% (w/v) of the test compound;
   b. Prepare vehicle control solution of equal volumes of acetone and ethanol;
   c. Prepare control solution of 0.01% (w/v) PMA in a mixture of equal volumes of acetone and ethanol, containing 1% dexamethasone;
   d. Divide mice into groups of 3;
   e. Treat each group of mice by applying 20 µL of one of the above solutions to the right ear using a micropipetter;
   f. Wait 6 hours and euthanize the mice in a $CO_2$ chamber;
   g. Cut the ears and punch out circles of 6-mm diameter;
   h. Measure the weight of three appropriate ear punches in the same group together;
   i. Determine the average weight of all untreated ear samples (average weight of control ear);
   j. Determine the average weight of each group of test ear samples (average weight of test ear);
   k. Calculate average % increase in ear weight as follows:

Average % increase in ear weight =

$$\frac{(\text{Average weight of test ear}) - (\text{Average weight of control ear})}{(\text{Average weight of control ear})} \times 100$$

3. Results are illustrated in FIG. 1. At 5%, CPR-2006 inhibits PMA-induced ear inflammation as effectively as 1% dexamethasone. Menthol, however, does not inhibit PMA-induced ear edema at concentrations up to 5%. Dexamethasone is a known anti-inflammatory steroid. Menthol is the parent compound which has been phosphocholinated. Without the phosphocholine group, it is not anti-inflammatory.

The positive results obtained in the foregoing in vivo assay are illustrative of the anti-inflammatory activity of the Formula I compounds. These compounds thus have utility in treating those disease states where inflammation is a contributing or major factor, such as in bronchial asthma, rheumatoid arthritis, osteoarthritis, psoriasis, and immediate and delayed-type hypersensitivity reactions.

The instant invention thus provides a method of treating inflammation in a mammal afflicted with same comprising administering to said mammal an effective anti-inflammatory amount of a compound of Formula I or a pharmaceutically-acceptable salt thereof. It also provides pharmaceutical compositions comprising an effective anti-inflammatory amount of a compound of Formula I or a pharmaceutically-acceptable salt thereof and a pharmaceutically-acceptable carrier.

II. ANTI-ARRHYTHMIC

The anti-arrhythmic activity of the Formula I compounds and pharmaceutically-acceptable salts thereof may be assayed by conventional methodologies such as the following:

In Vivo Assay: Acetylcholine-Induced Atrial Tachyarrhythmia Model

Compounds with potential anti-arrhythmic activity can be evaluated in animal models in which atrial fibrillation is induced by acetylcholine (T. P. Pruss and W. E. Hageman, "Acetylcholine-Induced Atrial Tachyarrhythmia: A Modification to Quantitative Potency and Duration",*Experientia* 1973,29:1449–1450). A detailed protocol is described in said reference. The pig is used as the animal species in this evaluation. The marked anti-arrhythmic activity of the Formula I compounds is demonstrated by using CPR-2006 as the test compound.

1. Methodology:
   a. Perform a right-sided thoracotomy at the 4th interspace of an anesthetized pig;
   b. Incise the pericardium over the right atrium;
   c. Suture the incised pericardium to the thoracic wall;
   d. Place 4–6 drops of a 10% solution of acetylcholine in saline on the right atrium;
   e. After 20 seconds, stroke the right atrium gently with a spatula to induce fibrillation;

f. Determine the period of atrial fibrillation;

g. Allow 10 minutes between the reversion to normal sinus rhythm and the induction of the next fibrillation;

h. Dissolve the test compound in saline at 50 mg/mL;

i. To evaluate the anti-arrhythmic effect of the test compound, inject the compound dissolved in saline at 1.1, 2.7, 5.5 or 10 mg/kg intravenously 10 seconds after the induction of fibrillation, and determine the duration of fibrillation.

Figure 2:
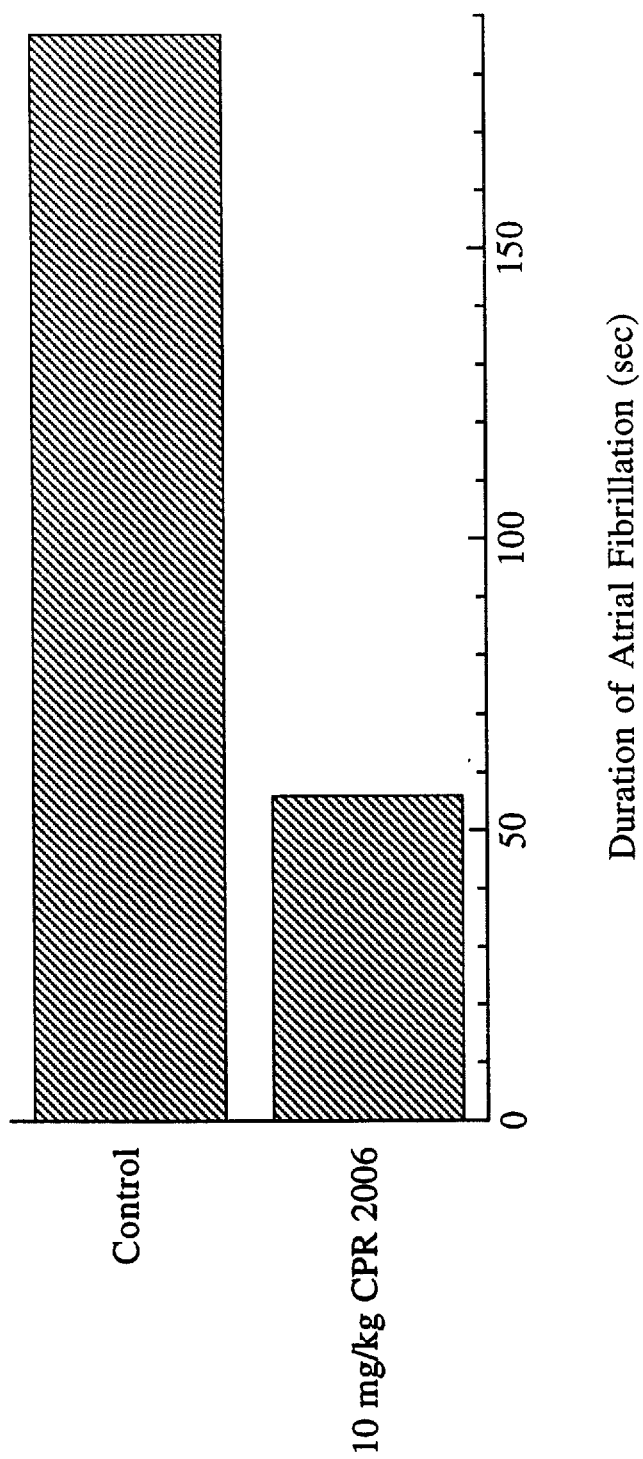
FIG. 2 is a graphical representation of results of an in vivo assay evaluating the decrease in duration of atrial fibrillation in a pig by CPR-2006.

2. The results, presented in FIG. 2, demonstrate that i.v. treatment with 10 mg/kg of CPR-2006 dramatically decreases the duration of atrial fibrillation. Further attempts to induce arrhythmia by stroking the right atrium resulted in only momentary fibrillation and immediate reversion to normal rhythm. A dose-response experiment is then conducted to confirm the anti-arrhythmic activity of CPR-2006. Results, which are presented in the following Table 1, indicate that i.v. treatment with 5.5 mg/kg CPR-2006 dramatically decreases the duration of atrial fibrillation. Fourteen minutes after the administration of 5.5 mg/kg CPR-2006, all attempts to induce atrial fibrillation fail.

TABLE 1

Acetylcholine-Induced Atrial Fibrillation in Pig

| Dose of CPR 2006 | Duration of Atrial Fibrillation |
| --- | --- |
| 0 | 7 min + 5 sec |
| 0 | 5 min + 39 sec |
| 1.1 mg/kg | 5 min + 27 sec |
| 2.7 mg/kg | 6 min + 51 sec |
| 5.5 mg/kg | 1 min + 59 sec |
| Re-induced fibrillation by stroking the right atrium: | |
| 3 min after the last dose | 1 min + 10 sec |
| 14 min after the last dose | 0 |

In view of the anti-arrhythmic activity of the subject compounds I, they can be utilized to treat chronic or acute arrhythmic conditions such as atrial fibrillation, atrial flutter, ventricular extrasystole, ventricular tachycardia, as well as to prevent ventricular fibrillation.

III. LOCAL ANALGESIA:

Studying the corneal reflex is a common method for evaluating compounds with potential local anesthetic activity (M.R.A. Chance and H. Lobstein "The Value Of The Guinea-Pig Corneal Reflex for Tests of Surface Anaesthesia" *J. Pharmacol. Exp. Ther.* 1944, 82:203–210). CPR 2006 is evaluated as a potential local anesthetic agent using this method. The animal species used in this evaluation is the pig.

1. Methodology:

a. The pig is tranquilized with ketamine and azaperone to alleviate discomfort;

b. Keep eyelids of one eye open using a surgical retractor;

c. Bring a soft pointed sponge in brief contact with the cornea several times to observe normal corneal reflexes;

d. Prepare a 5% solution of CPR 2006 in saline;

e. Place four drops of the above solution in the eye under study;

f. Test the corneal reflex every five minutes by bringing the sponge in contact with the cornea.

2. Fifteen minutes after the addition of CPR 2006 to the eye, contact between the sponge and the cornea does not induce a reflex, demonstrating CPR 2006 has local anesthetic activity.

In view of the local anesthetic activity of the subject compounds, it is evident that the present invention provides a method of preventing or alleviating topical pain and topical pruritus, that is, providing topical analgesia, in warm-blooded mammals, including humans, for example, by the topical administration of an effective local anesthetic amount of a compound of Formula I or a pharmaceutically-acceptable isomer or salt thereof in admixture with a pharmaceutical carrier.

PHARMACEUTICAL COMPOSITIONS

Another aspect of the invention provides pharmaceutical compositions, for medical use, comprising an active compound, i.e., a Formula I compound or a pharmaceutically-acceptable salt thereof, together with an acceptable carrier therefor and optionally other therapeutically active ingredients. The carrier must be pharmaceutically-acceptable in the sense of being compatible with the other ingredients of the formulation and not deleterious to the recipient thereof. The compositions include those suitable for oral, topical, inhalation, rectal or parenteral (including subcutaneous, intramuscular and intravenous) administration. Preferred are those suitable for oral, topical, parenteral, inhalation or rectal administration.

The formulations may conveniently be presented in unit dosage form and may be prepared by any of the methods well known in the art of pharmacy. The term "unit dosage" or "unit dose" is denoted to mean a predetermined amount of the active ingredient sufficient to be effective for treating each of the indicated activities. All methods include the step of bringing the active compound into association with a carrier and one or more optional accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulation suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solution or solids containing the compound of Formula I which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the compounds of formula I are preferable utilized at a concentration of from about 0.1% to 5.0% by weight.

Compositions suitable for rectal administration, preferably for the treatment of hemorrhoids and the like, comprise a suppository, preferably bullet-shaped, containing the active ingredient and pharmaceutically-acceptable vehicles therefore such as hard fat, hydrogenated cocoglyceride, polyethylene glycol and the like. In suppository formulations, the compounds of Formula (I) are preferably utilized at concentrations of from about 0.1% to 10% by weight.

Compositions suitable for rectal administration, preferred for the treatment of ulcerative colitis and the like, also comprise a rectal enema unit containing the active ingredient and pharmaceutically-acceptable vehicles therefore such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the compounds of Formula (I) are preferably utilized at concentrations of from about 5.0–10% by weight. Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of compounds of Formula I are preferable utilized at concentrations of from about 0.1% to 5.0% by weight applied to a dressing.

Compositions suitable for administration by inhalation to treat, for example, acute or chronic bronchial asthma, include formulations wherein the active ingredient is a solid or liquid admixed in a micronized powder having a particle size in the range of about 5 microns or less to about 500 microns or liquid formulations in a suitable diluent. These formulations are designed for rapid inhalation through the oral passage from a conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of compound of Formula I required to be effective for each of the indicated activities will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. In general, a suitable effective dose is in the range of about 0.5 to about 500 mg/kg body weight per day, preferably in the range of about 5 to about 350 mg/kg per day, calculated as the non-salt form of Formula I. The total daily dose may be given as a single dose, multiple doses, e.g., two to six times per day, or by intravenous infusion for a selected duration. Dosages above or below the range cited above are within the scope of the present invention and may be administered to the individual patient if desired and necessary. Dosages above or below the range cited above are within the scope of the present invention and may be administered to the individual patient if desired and necessary. In general, the pharmaceutical compositions of this invention contain from about 0.5 mg to about 15 g and, preferably, from about 7.5 to about 1500 mg per day, and a typical dose would be about 800 mg per day. If discrete multiple doses are indicated, treatment might typically be 200 mg of a compound of Formula I given 4 times per day.

EXAMPLES

The following examples are included to illustrate and not to limit the scope of the present invention. Examples 1 and 2 are illustrative of Step 1 in Reaction Scheme 1. Example 3 and 4 are illustrative of Step 1 in Reaction Scheme 2. Examples 5–10 are illustrative of Steps 1 and 2 in Reaction Scheme 3. Examples 11–20 are illustrative of Steps 1–3 in Reaction Scheme 4. Examples 21–28 are illustrative of Steps 1–2 in Reaction Scheme 5.

Example 1

(1R, 2S, 5R)-Menthylphosphocholine (L-menthylphosphocholine, CPR-2006): illustrative of Step 1 in Reaction Scheme 1.

Neat 2-chloro-2-oxo-1,3,2-dioxaphospholane (15.0 g, 0.105 mol) is added in one portion to a stirred mixture of (1R, 2S, 5R)-(−)-menthol (L-menthol, 15 g, 0.096 mol) and triethylamine (29.5 mL, 0.212 mol) in anhydrous toluene (560 mL) under a nitrogen atmosphere at room temperature. The resultant mixture is stirred at room temperature for four days. The white solid which precipitates is filtered and washed with dry toluene (100 mL). The toluene filtrate is concentrated in vacuo to leave a viscous residue which is further dried under high vacuum. Then, a mixture of trimethylamine (52.2 g) in acetonitrile (dried by distillation over phosphorus pentoxide, 600 mL) is added to the residue. The flask which contains the residue and trimethylamine in acetonitrile is sealed by tightly connecting glass stoppers with wire and is then heated with stirring to 60°–70° C. for 24 hours. Upon cooling, a white solid precipitates. The flask which contains the reaction mixture is then placed in a refrigerator for 24 hours to further crystallize. The white solid precipitate is filtered from the cold solution and is washed sequentially with dry acetonitrile and acetone. The white, crystalline (1R, 2S, 5R)-menthylphosphocholine is dried under vacuum to provide 15.692 g (50.9%): TLC (silica gel 60) 70:30:5 $CHCl_3$—$CH_3OH$—30% aqueous ammonia ($R_f$=0.25); mp 245°–246° C.

Example 2

By following the procedure outlined in Example 1, except that an equivalent amount of the appropriate R-O-H is employed as the starting material, the following representative compounds of Formula (B) are obtained: cyclopentylphosphocholine, (trans-2-methylcyclopentyl)- phosphocholine, (cis-2-methylcyclopentyl)-phosphocholine, cyclohexyl-phosphocholine, isopulegyl-phosphocholine, cycloheptyl-phosphocholine, phenyl-phosphocholine, ortho-cresyl-phosphocholine, (3-ethylphenyl)-phosphocholine, (2-propylphenyl)-phosphocholine, (2-iso-propylphenyl)-phosphocholine, (2,5-dimethylphenyl)-phosphocholine, (3-iso-propylphenyl)-phosphocholine, thymyl-phosphocholine, carvacryl-phosphocholine, (3-methylcyclohexyl)-phosphocholine, and (2-ethylcyclohexyl)-phosphocholine.

Example 3

Cyclopentylphosphoethanolamine: illustrative of Step 1 of Reaction Scheme 2.

A mixture of anhydrous tetrahydrofuran (THF, 40 mL) and phosphorus oxychloride (36.8 g, 240 mmol) is cooled to 0° C. Into this stirred solution, a mixture of 17.23 g (200 mmol) of cyclopentanol, triethylamine (36.4 g, 360 mmol) and THF (240 mL) is added dropwise as the temperature is maintained at 0°–4° C. Some material precipitates. The cooling device is removed, and a mixture of ethanolamine (14.7 g, 240 mmol), triethylamine (36.4 g, 360 mmol) and THF (180 mL) is added to the stirred solution within 5 minutes. The temperature rises to about 55° C. and stirring is continued at this temperature for one hour. After cooling the reaction mixture to 15° C., a solution of concentrated aqueous HCl (approximate 12N, 30 mL) and water (170 mL) is added to the reaction mixture at 25°–30° C. The reaction mixture is allowed to come to ambient temperature and stirring is continued for one hour. The water layer is removed, and then the THF layer is diluted with methylene dichloride (600 mL). Sodium bicarbonate (50 g) is then added with vigorous stirring. After stirring is continued for 15 minutes, anhydrous sodium sulfate is added and stirring is resumed for a few minutes. The inorganic material is removed by filtration, and the solvent is evaporated under reduced pressure. The residue is taken up in methylene dichloride (500 mL), and the slight turbidity in the resultant solution is removed by swirling with charcoal followed by filtration of the charcoal with a glass filter. Approximately half of the volume of the methylene dichloride mixture is removed in vacuo, and acetone (200 mL) is then added to the concentrated methylene dichloride mixture. Upon cooling to 0° C. for two hours, 39.3 g (94%) of crude product precipitates. This material is dissolved in boiling 2-propanol, and then the solution is passed through a filter and cooled to room temperature. On standing overnight at room temperature, crystalline cyclopentylphosphoethanolamine is obtained and purified by chromatography. TLC: 65:25:5 $CHCl_3$—$CH_3OH$—$H_2O$; $R_f$=0.22

Example 4

By following the procedure outlined in Example 3, except that an equivalent amount of the appropriate of R-O-H is employed as the starting material, the following representative compounds of Formula (C) are obtained: (trans-2-methylcyclopentyl)-phosphoethanolamine, (cis-2-methylcyclopentyl)-phosphoethanolamine, cyclohexyl-phosphoethanolamine, isopulegyl-phosphoethanolamine, cycloheptyl-phosphoethanolamine, phenyl-phosphoethanolamine, ortho-cresyl-phosphoethanolamine, (3-ethylphenyl)-phosphoethanolamine, (2-propylphenyl)-phosphoethanolamine, (2-iso-propylphenyl)-phosphoethanolamine, (2,5-dimethylphenyl)-phosphoethanolamine, (3-iso-propylphenyl)-phosphoethanolamine, thymyl-phosphoethanolamine, carvacryl-phosphoethanolamine, (3-methylcyclohexyl)-phosphoethanolamine, menthylphosphoethanolamine and (2-ethylcyclohexyl)-phosphoethanolamine.

Example 5

Thymyl-2-thio-1,3,2-dithiaphospholane: illustrative of Step 1 of Reaction Scheme 3.

A solution of 2-chloro-1,3,2-dithiaphospholane (3.17 g, 20 mmol) in acetonitrile (20 mL) is added dropwise to a stirred solution of thymol (3.0 g, 20 mmol) and N,N-diisopropylethylamine (2.84 g, 22 mmol) in anhydrous, oxygen-free acetonitrile (200 mL) at −38° C. After stirring for 4 h at −38° C., the reaction mixture is warmed to room temperature and is stirred for an additional 2 h at room temperature. A solution of elemental sulfur (3.2 g, 100 mmol) in carbon disulfide (100 mL) is then added, and the resultant light yellow heterogeneous mixture is stirred vigorously for 8 h. The reaction mixture is concentrated under reduced pressure and then is dissolved in ethyl acetate (EtOAc, 100 mL). The yellow flocculant solid that forms is removed by filtration. The filtrate is concentrated under reduced pressure, and the residue is purified by flash chromatography using acetone-chloroform-water as the eluent to give the named product.; TLC: $CHCl_3$; $R_f$=0.5.

Example 6

By following the procedure outlined in Example 5, except that an equivalent amount of the appropriate R-O-H is employed as the starting material, the following representative compounds of Formula (D) are obtained: cyclopentyl-2-thio-1,3,2-dithiaphospholane, (trans-2-methylcyclopentyl)-2-thio-1,3,2-dithiaphospholane, (cis-2-methylcyclopentyl)-2-thio-1,3,2-dithiaphospholane, cyclohexyl-2-thio-1,3,2-dithiaphospholane, isopulegyl-2-thio-1,3,2-dithiaphospholane, cycloheptyl-2-thio-1,3,2-dithiaphospholane, phenyl-2-thio-1,3,2-dithiaphospholane, ortho-cresyl-2-thio-1,3,2-dithiaphospholane, (3-ethylphenyl)-2-thio-1,3,2-dithiaphospholane, (2-propylphenyl)-2-thio-1,3,2-dithiaphospholane, (2-iso-propylphenyl)-2-thio-1,3,2-dithiaphospholane, (2,5-dimethylphenyl)-2-thio-1,3,2-dithiaphospholane, (3-iso-propylphenyl)-2-thio-1,3,2-dithiaphospholane, menthyl-2-thio-1,3,2-dithiaphospholane, carvacryl-2-thio-1,3,2-dithiaphospholane, (3-methylcyclohexyl)-2-thio-1,3,2-dithiaphospholane, and (2-ethylcyclohexyl)-2-thio-1,3,2-dithiaphospholane.

Example 7

Thymyl-dithiophosphocholine: illustrative of Step 2 in Reaction Scheme 3.

In one portion 1,8-diazabicyclo(5.4.0)undec-7-ene (DBU, 2.0 g, 13.1 mmol) is added to a stirred solution of choline p-toluenesulfonate (3.61 g, 13.1 mmol) and thymyl-2-thio-1,3,2-dithiaphospholane (4.0 g, 13.1 mmol) in anhydrous acetonitrile (120 mL) at room temperature. The solution is stirred at room temperature for 1 hour and then concentrated in vacuo. The crude product is purified by flash chromatography 6.7:3.2:0.1 acetone chloroform:water to give thymyl-dithiophosphocholine. TLC: 65:25:5 $CHCl_3$—$CH_3OH$—$H_2O$; $R_f$=0.24.

Example 8

By following the procedure outlined in Example 7, except that an equivalent amount of the appropriate R-O-2-thio-1, 3,2-dithiaphospholane of Formula (D) is employed as the starting material, the following representative compounds of Formula (E), where $R^3$ is methyl, are obtained: cyclopentyl-dithiophosphocholine, (trans-2-methylcyclopentyl)- dithiophosphocholine, (cis-2-methylcyclopentyl)-dithiophosphocholine, cyclohexyl-dithiophosphocholine, isopulegyl-dithiophosphocholine, cycloheptyl-dithiophosphocholine, phenyl-dithiophosphocholine, ortho-cresyl-dithiophosphocholine, (3-ethylphenyl)-dithiophosphocholine, (2-propylphenyl)-dithiophosphocholine, (2-iso-propylphenyl)-dithiophosphocholine, (2,5-dimethylphenyl)-dithiophosphocholine, (3-iso-propylphenyl)-dithiophosphocholine, menthyl-dithiophosphocholine, carvacryl-dithiophosphocholine, (3-methylcyclohexyl)-dithiophosphocholine, and (2-ethylcyclohexyl)-dithiophosphocholine.

Example 9
Thymyl-dithiophospho-(N,N-dimethylethanolamine): illustrative of Step 2 in Reaction Scheme 3.

In one portion 1,8-diazabicyclo(5.4.0)undec-7-ene (DBU, 2.0 g, 13.1 mmol) is added to a stirred solution of N,N-dimethylethanolamine (1.17 g, 13.1 mmol) and thymyl-2-thio-1,3,2-dithiaphospholane (4.0 g, 13.1 mmol) in anhydrous acetonitrile (120 mL) at room temperature. The solution is stirred at room temperature for 1 hour and then concentrated in vacuo. The crude product is purified by flash chromatography 6.7:3.2:0.1 acetone chloroform:water to give thymyl-dithiophospho-(N,N-dimethylethanolamine). TLC: 65:25:5 $CHCl_3$—$CH_3OH$-$H_2O$; $R_f$=0.22.

Example 10

By following the procedure outlined in Example 9, except that an equivalent amount of the appropriate R-O-2-thio-1,3,2-dithiaphospholane of Formula (D) is employed as the starting material, the following representative compounds of Formula (E), where $R^3$=hydrogen, are obtained: cyclopentyl-dithiophospho-(N,N-dimethylethanolamine), (trans-2-methylcyclopentyl)-dithiophospho-(N,N-dimethylethanolamine), (cis-2-methylcyclopentyl)-dithiophospho-(N,N-dimethylethanolamine), cyclohexyl-dithiophospho-(N,N-dimethylethanolamine), isopulegyl-dithiophospho-(N,N-dimethylethanolamine), cycloheptyl-dithiophospho-(N,N-dimethylethanolamine), phenyl-dithiophospho-(N,N-dimethylethanolamine), ortho-cresyl-dithiophospho-(N,N-dimethylethanolamine), (3-ethylphenyl)-dithiophospho-(N,N-dimethylethanolamine), (2-propylphenyl)-dithiophospho-(N,N-dimethylethanolamine), ( 2-iso-propylphenyl)-dithiophospho-(N,N-dimethylethanolamine), (2,5-dimethylphenyl)-dithiophospho-(N,N-dimethylethanolamine), (3-iso-propylphenyl)-dithiophospho-(N,N-dimethylethanolamine), menthyl-dithiophospho-(N,N-dimethylethanolamine), carvacryl-dithiophospho-(N,N-dimethylethanolamine), (3-methylcyclohexyl)-dithiophospho-(N,N-dimethylethanolamine), and (2-ethylcyclohexyl)-dithiophospho-(N,N-dimethylethanolamine).

Example 11
(2-Methylcyclohexyl)-2-thio-1,3,2-dithiaphospholane: illustrative of Step 1 in Reaction Scheme 4.

A solution of 2-chloro-1,3,2-dithiaphospholane (47.6 g, 300 mmol) in acetonitrile (270 mL) is added dropwise to a stirred solution of 2-methylcyclohexanol (34.3 g, 300 mmol) and N,N-diisopropylethylamine (42.65 g, 330 mmol) in anhydrous, oxygen-free acetonitrile (2.7 L) at −38° C. After stirring for 8 h at −38° C., the reaction mixture is warmed to room temperature and is vigorously stirred for an additional 4 h at room temperature. A solution of elemental sulfur (48 g, 1.5 mol) in carbon disulfide (1.5 L) is then added, and the resultant light yellow heterogeneous mixture is stirred vigorously for 12 h. The reaction mixture is concentrated under reduced pressure and then is dissolved in EtOAc (3 L). The yellow flocculant solid that forms is removed by filtration. The filtrate is concentrated under reduced pressure, and the residue is purified by flash chromatography using acetone-chloroform-water as the eluent to give the named product.; TLC: $CHCl_3$; $R_f$=0.5.

Example 12

By following the procedure outlined in Example 11, except that an equivalent amount of the appropriate R-O-H is employed as the starting material, the following representative compounds of Formula (D) are obtained: cyclopentyl-2-thio-1,3,2-dithiaphospholane, menthyl-2-thio-1,3,2-dithiaphospholane, cyclohexyl-2-thio-1,3,2-dithiaphospholane, isopulegyl-2-thio-1,3,2-dithiaphospholane, cycloheptyl-2-thio-1,3,2-dithiaphospholane, phenyl-2-thio-1,3,2-dithiaphospholane, ortho-cresyl-2-thio-1,3,2-dithiaphospholane, (3-ethylphenyl)-2-thio-1,3,2-dithiaphospholane, (2-propylphenyl)-2-thio-1,3,2-dithiaphospholane, (2-iso-propylphenyl)-2-thio-1,3,2-dithiaphospholane, (2,5-dimethylphenyl)-2-thio-1,3,2-dithiaphospholane, (3-iso-propylphenyl)-2-thio-1,3,2-dithiaphospholane, thymyl-2-thio-1,3,2-dithiaphospholane, carvacryl-2-thio-1,3,2-dithiaphospholane, (3-methylcyclohexyl)-2-thio-1,3,2-dithiaphospholane, and (2-ethylcyclohexyl)-2-thio-1,3,2-dithiaphospholane.

Example 13
(2-Methylcyclohexyl)-dithiophospho-(N-tert-butoxycarbonyl)ethanolamine: illustrative of Step 2 in Reaction Scheme 4.

In one portion 1,8-diazabicyclo(5.4.0)undec-7-ene (DBU, 5.68 g, 37.3 mmol) is added to a stirred solution of N-(tert-butoxycarbonyl)ethanolamine (6.01 g, 37.3 mmol) and (2-methylcyclohexyl)-2-thio-1,3,2-dithiaphospholane (10.0 g, 37.3 mmol) in anhydrous acetonitrile (350 mL) at room temperature. The solution is stirred at room temperature for 2 hours and then concentrated in vacuo. The crude product is purified by flash chromatography to give (2-methylcyclohexyl)-dithiophospho-(N-tert-butoxycarbonyl)ethanolamine; TLC: 65:25:5 $CHCl_3$—$CH_3OH$—$H_2O$; $R_f$=0.69.

Example 14

By following the procedure outlined in Example 13, except that an equivalent amount of the appropriate R-O-2-thio-1,3,2-dithiaphospholane of Formula (D) is employed as the starting material, the following representative compounds of Formula (F), where $R^3$ is hydrogen, are obtained: cyclopentyl-dithiophospho-(N-tert-butoxycarbonylethanolamine), (trans-2-methylcyclopentyl)-dithiophospho-(N-tert-butoxycarbonylethanolamine), (cis-2-methylcyclopentyl)-dithiophospho-(N-tert-butoxycarbonylethanolamine), cyclohexyl-dithiophospho-(N-tert-butoxycarbonylethanolamine), isopulegyl-dithiophospho-(N-tert-butoxycarbonylethanolamine), cycloheptyl-dithiophospho-(N-tert-butoxycarbonylethanolamine), phenyl-dithiophospho-(N-tert-butoxycarbonylethanolamine), ortho-cresyl-dithiophospho-(N-tert-butoxycarbonylethanolamine), (3-ethylphenyl)-dithiophospho-(N-tert-butoxycarbonylethanolamine), (2-propylphenyl)-dithiophospho-(N-tert-butoxycarbonylethanolamine), (2-iso-propylphenyl)-dithiophospho-(N-tertbutoxycarbonylethanolamine), (2,5-dimethylphenyl)-dithiophospho-(N-tert-butoxycarbonylethanolamine), (3-iso-propylphenyl)-dithiophospho-(N-tert-butoxycarbonylethanolamine), thymyl-dithiophospho-(N-tert-butoxycarbonylethanolamine), carvacryl-dithiophospho-(N-tert-butoxycarbonylethanolamine), (3-methylcyclohexyl)-dithiophospho-(N-tert-butoxycarbonylethanolamine), and (2-ethylcyclohexyl)-dithiophospho-(N-tert-butoxycarbonylethanolamine).

Example 15

(2-Methylcyclohexyl)-dithiophospho-(N-tert-butoxycarbonyl-N-methyl-ethanolamine): illustrative of Step 2 in Reaction Scheme 4.

In one portion 1,8-diazabicyclo(5.4.0)undec-7-ene (DBU, 9.64 g, 63.3 mmol) is added to a stirred solution of N-(tert-butoxycarbonyl-N-methyl)ethanolamine (11.09 g, 63.3 mmol) and thymyl-2-thio-1,3,2-dithiaphospholane (17.0 g, 63.3 mmol) in anhydrous acetonitrile (500 mL) at room temperature. The solution is stirred at room temperature for 4 hours and then concentrated in vacuo. The crude product is purified by flash chromatography to give (2-methylcyclohexyl)-dithiophospho-(N-tert-butoxycarbonyl-N-methyl-ethanolamine); TLC: 65:25:5 $CHCl_3$—$CH_3OH$—$H_2O$; $R_f$=0.64.

Example 16

By following the procedure outlined in Example 15, except that an equivalent amount of the appropriate R-O-2-thio-1,3,2-dithiaphospholane of Formula (D) is employed as the starting material, the following representative compounds of Formula (F), where $R^3$ is methyl, are obtained: cyclopentyl-dithiophospho-(N-tert-butoxy-carbonyl-N-methyl-ethanolamine), menthyl-dithiophospho-(N-tert-butoxy-carbonyl-N-methyl-ethanolamine), cyclohexyl-dithiophospho-(N-tert-butoxy-carbonyl-N-methyl-ethanolamine), isopulegyl-dithiophospho-(N-tert-butoxy-carbonyl-N-methyl-ethanolamine), cycloheptyl-dithiophospho-(N-tert-butoxy-carbonyl-N-methyl-ethanolamine), phenyl-dithiophospho-(N-tert-butoxy-carbonyl-N-methyl-ethanolamine), ortho-cresyl-dithiophospho-(N-tert-butoxy-carbonyl-N-methyl-ethanolamine), (3-ethylphenyl)-dithiophospho-(N-tert-butoxy-carbonyl-N-methyl-ethanolamine), (2-propylphenyl)-dithiophospho-(N-tert-butoxy-carbonyl-N-methyl-ethanolamine), (2-iso-propylphenyl)-dithiophospho-(N-tert-butoxy-carbonyl-N-methyl-ethanolamine), (2,5-dimethylphenyl)-dithiophospho-(N-tert-butoxy-carbonyl-N-methyl-ethanolamine), (3-iso-propylphenyl)-dithiophospho-(N-tert-butoxy-carbonyl-N-methyl-ethanolamine), thymyl-dithiophospho-(N-tert-butoxy-carbonyl-N-methyl-ethanolamine), carvacryl-dithiophospho-(N-tert-butoxy-carbonyl-N-methyl-ethanolamine), (3-methylcyclohexyl)-dithiophospho-(N-tert-butoxy-carbonyl-N-methyl-ethanolamine), and (2-ethylcyclohexyl)-dithiophospho-(N-tert-butoxy-carbonyl-N-methyl-ethanolamine).

Example 17

(2-Methylcyclohexyl)-dithiophosphoethanolamine: illustrative of Step 3 in Reaction Scheme 4.

A mixture of (2-methylcyclohexyl)-dithiophospho-(N-tert-butoxycarbonyl)ethanolamine (5.0 g, 13.5 mmol) and 2.8M aqueous HF (4.8 mL) in acetonitrile (12 mL) is stirred for 30 minutes at room temperature. The reaction is quenched by addition of 1N NaOH until the pH of the reaction mixture is 7. The resultant mixture is concentrated in vacuo and then column chromatographed to give (2-methylcyclohexyl)-dithiophosphoethanolamine; TLC: 65:35:5 $CHCl_3$—$CH_3OH$—$H_2O$; $R_f$=0.77.

Example 18

By following the procedure outlined in Example 17, except that an equivalent amount of the appropriate R-O-dithiophospho-(N-tert-butoxycarbonyl)ethanolamine is employed as the starting material, the following representative compounds of Formula (G), where $R^3$ is hydrogen, are obtained: cyclopentyl-dithiophosphoethanolamine, menthyl-dithiophosphoethanolamine, cyclohexyl-dithiophosphoethanolamine, isopulegyl-dithiophosphoethanolamine, cycloheptyl-dithiophosphoethanolamine, phenyl-dithiophosphoethanolamine, ortho-cresyl-dithiophosphoethanolamine, (3-ethylphenyl)-dithiophosphoethanolamine, (2-propylphenyl)-dithiophosphoethanolamine, (2-iso-propylphenyl)-dithiophosphoethanolamine, (2,5-dimethylphenyl)-dithiophosphoethanolamine, (3-iso-propylphenyl)-dithiophosphoethanolamine, thymyl-dithiophosphoethanolamine, carvacryl-dithiophosphoethanolamine, (3-methylcyclohexyl)-dithiophosphoethanolamine, and (2-ethylcyclohexyl)-dithiophosphoethanolamine.

Example 19

(2-Methylcyclohexyl)-dithiophospho-(N-methyl-ethanolamine): illustrative of Step 3 in Reaction Scheme 4.

A mixture of (2-methylcyclohexyl)-dithiophospho-(N-tert-butoxycarbonyl-N-methyl)ethanolamine (5.0 g, 13.0 mmol) and 2.8M aqueous HF (4.6 mL) in acetonitrile (12 mL) is stirred for 30 minutes at room temperature. The reaction is quenched by addition of 1N NaOH until the pH of the reaction mixture is 7. The resultant mixture is concentrated in vacuo and then column chromatographed to give (2-methylcyclohexyl)-dithiophospho-(N-methyl) ethanolamine; TLC: 65:35:5 $CHCl_3$—$CH_3OH$—$H_2O$; $R_f$=0.80.

Example 20

By following the procedure outlined in Example 19, except that an equivalent amount of the appropriate R-O-dithiophospho-(N-tert-butoxycarbonyl-N-methyl)ethanolamine is employed as the starting material, the following representative compounds of Formula (G), where $R^3$ is methyl, are obtained: cyclopentyl-dithiophospho-(N-methyl-ethanolamine), menthyl-dithiophospho-(N-methyl-ethanolamine), cyclohexyl-dithiophospho-(N-methyl-ethanolamine), isopulegyl-dithiophospho-(N-methyl-ethanolamine), cycloheptyl-dithiophospho-(N-methyl-ethanolamine), phenyl-dithiophospho-(N-methyl-ethanolamine), ortho-cresyl-dithiophospho-(N-methyl-ethanolamine), (3-ethylphenyl)-dithiophospho-(N-methyl-ethanolamine), (2-propylphenyl)-dithiophospho-(N-methyl-ethanolamine), (2-iso-propylphenyl)-dithiophospho-(N-methyl-ethanolamine), (2,5-dimethylphenyl)-dithiophospho-(N-methyl-ethanolamine), (3-iso-propylphenyl)-dithiophospho-(N-methyl-ethanolamine), thymyl-dithiophospho-(N-methyl-ethanolamine), carvacryl-dithiophospho-(N-methyl-ethanolamine), (3-methylcyclohexyl)-dithiophospho-(N-methyl-ethanolamine), and (2-ethylcyclohexyl)-dithiophospho-(N-methyl-ethanolamine).

Example 21

(3-Methylcyclohexyl)-thiophosphoryl dichloride: illustrative of Step 1 in Reaction Scheme 5.

A mixture of 3-methylcyclohexanol (5.0 g, 43.8 mmol) in trichloroethylene (300 mL) is added dropwise to a 0°–4° C. mixture of thiophosphoryl chloride (11.13 g, 65.7 mmol) and anhydrous pyridine (5.20 g, 65.7 mmol) in trichloroethylene (125 mL) over a 1 hour period under a nitrogen atmosphere. The resultant reaction mixture is stirred at 0°–4° C. for 1 hour and is then warmed to room temperature and stirred at room temperature for 8 hours. A white solid gradually precipitates. The white solid is filtered from the reaction mixture. The resultant reaction mixture is concentrated in vacuo to a residue. Successive aliquots of toluene (100 mL) are added to the residue and then separately are evaporated in vacuo to give 7.57 g (70%) of (3-methylcyclohexyl)-thiophosphoryl dichloride which can be used directly without further purification as the starting material for Example 23.

Example 22

By following the procedure outlined in Example 21, except that an equivalent amount of the appropriate R-O-H is employed as the starting material, the following representative compounds of Formula (H) are obtained: cyclopentyl-thiophosphoryl dichloride, (trans-2-methylcyclopentyl)-thiophosphoryl dichloride, (cis-2-methylcyclopentyl)-thiophosphoryl dichloride, cyclohexyl-thiophosphoryl dichloride, isopulegyl-thiophosphoryl dichloride, cycloheptyl-thiophosphoryl dichloride, phenyl-thiophosphoryl dichloride, ortho-cresyl-thiophosphoryl dichloride, (3-ethylphenyl)-thiophosphoryl dichloride, (2-propylphenyl)-thiophosphoryl dichloride, (2-iso-propylphenyl)-thiophosphoryl dichloride, (2,5-dimethylphenyl)-thiophosphoryl dichloride, (3-iso-propylphenyl)-thiophosphoryl dichloride, thymyl-thiophosphoryl dichloride, carvacryl-thiophosphoryl dichloride, (3-methylcyclohexyl)-thiophosphoryl dichloride, and (2-ethylcyclohexyl)-thiophosphoryl dichloride.

Example 23
(3-Methylcyclohexyl)-thiophosphocholine: illustrative of Step 2 in Reaction Scheme 5.

A solution of ethanolamine (2.74 g, 16.2 mmol) and pyridine (4.79 g, 60.6 mmol) in anhydrous tetrahydrofuran (100 mL) is added to a 0°–4° C. solution of (2-iso-propylphenyl)-thiophosphoryl dichloride (preparation is described in Example 21, 5.0 g, 20.3 mmol) in anhydrous tetrahydrofuran (100 mL) over a 1 hour period. The resultant reaction mixture is warmed to room temperature and is stirred at room temperature for 6 hours. The mixture is then filtered and concentrated in vacuo. The resultant residue is dissolved into a 1:1 (v/v) 2-propanol-tetrahydrofuran solution (250 mL) and then is stirred with a 20% (v/v) aqueous acetic acid solution (250 mL) at room temperature for 6 hours. The precipitated product is filtered and is purified by chromatography, followed by drying under vacuum, to give (3-methylcyclohexyl)-thiophosphoethanolamine; TLC (silica): 60:35:5 $CHCl_3$—$CH_3OH$—20% aqueous $NH_4OH$; $R_f$=0.72.

Example 24

By following the procedure outlined in Example 23, except that an equivalent amount of the appropriate R-O-thiophosphoryl dichloride is employed as the starting material, the following representative compounds of Formula I, where $R^3$ in OPEA is hydrogen, are obtained: cyclopentyl-thiophosphoryl dichloride, (trans-2-methylcyclopentyl)-thiophosphoryl dichloride, (cis-2-methylcyclopentyl)-thiophosphoryl dichloride, cyclohexyl-thiophosphoryl dichloride, isopulegyl-thiophosphocholine, cycloheptyl-thiophosphoryl dichloride, phenyl-thiophosphoryl dichloride, ortho-cresyl-thiophosphoryl dichloride, (3-ethylphenyl)-thiophosphoryl dichloride, (2-propylphenyl)-thiophosphoryl dichloride, (2-iso-propylphenyl)-thiophosphoryl dichloride, (2,5-dimethylphenyl)-thiophosphoryl dichloride, (3-iso-propylphenyl)-thiophosphoryl dichloride, thymyl-thiophosphoryl dichloride, carvacryl-thiophosphoryl dichloride, (3-methylcyclohexyl)-thiophosphocholine, and (2-ethylcyclohexyl)-thiophosphoryl dichloride.

Example 25
(2-iso-Propylphenyl)-thiophosphoryl dichloride: illustrative of Step 1 in Reaction Scheme 5.

A mixture of 2-iso-propylphenol (10.0 g, 73.4 mmol) in trichloroethylene (600 mL) is added dropwise to a 0°–4° C. mixture of thiophosphoryl chloride (18.63 g, 110 mmol) and anhydrous pyridine (8.70 g, 110 mmol) in trichloroethylene (250 mL) over a 1 hour period under a nitrogen atmosphere. The resultant reaction mixture is stirred at 0°–4° C. for 2 hours, is warmed to room temperature and then is stirred at room temperature for 12 hours. A white solid gradually precipitates. The white solid is filtered from the reaction mixture. The resultant reaction mixture is concentrated in vacuo to a residue. Successive aliquots of toluene (200 mL) are added to the residue and then separately evaporated in vacuo to give (2-iso-propylphenyl)-thiophosphoryl dichloride which can be used directly without further purification as the starting material for Example 27.

Example 26

By following the procedure outlined in Example 25, except that an equivalent amount of the appropriate R-O-H is employed as the starting material, the following representative compounds of Formula (H) are obtained: cyclopentyl-thiophosphoryl dichloride, (trans-2-methylcyclopentyl)-thiophosphoryl dichloride, (cis-2-methylcyclopentyl)-thiophosphoryl dichloride, cyclohexyl-thiophosphoryl dichloride, isopulegyl-thiophosphoryl dichloride, cycloheptyl-thiophosphoryl dichloride, phenyl-thiophosphoryl dichloride, ortho-cresyl-thiophosphoryl dichloride, (3-ethylphenyl)-thiophosphoryl dichloride, (2-propylphenyl)-thiophosphoryl dichloride, menthyl-thiophosphoryl dichloride, (2,5-dimethylphenyl)-thiophosphoryl dichloride, (3-iso-propylphenyl)-thiophosphoryl dichloride, thymyl-thiophosphoryl dichloride, carvacryl-thiophosphoryl dichloride, (3-methylcyclohexyl)-thiophosphoryl dichloride, and (2-ethylcyclohexyl)-thiophosphoryl dichloride.

Example 27
(2-iso-Propylphenyl)-thiophosphoethanolamine: illustrative of Step 2 in Reaction Scheme 5.

A solution of ethanolamine (1.82 g, 29.8 mmol) and pyridine (8.86 g, 112 mmol) in anhydrous tetrahydrofuran (200 mL) is added to a 0°–4° C. solution of (2-iso-propylphenyl)-thiophosphoryl dichloride (preparation is described in Example 25, 10.0 g, 37.2 mmol) in anhydrous tetrahydrofuran (200 mL) over a 2 hour period. The resultant reaction mixture is warmed to room temperature and is stirred at room temperature for 12 hours. The mixture is then filtered and concentrated in vacuo. The resultant residue is dissolved into a 1:1 (v/v) 2-propanol-tetrahydrofuran solution (450 mL) and is then stirred with a 20% (v/v) aqueous acetic acid solution (450 mL) at room temperature for 12 hours. The precipitated product is filtered and is purified by chromatography, followed by drying under vacuum, to give (2-iso-propylphenyl)-thiophosphoethanolamine; TLC (silica): 60:35:5 $CHCl_3$—$CH_3OH$—20% aqueous $NH_4OH$; $R_f$=0.75.

Example 28

By following the procedure outlined in Example 27, except that an equivalent amount of the appropriate R-O-thiophosphoryl dichloride is employed as the starting material, the following representative compounds of Formula I, where $R^3$ in OPEA are all methyl, are obtained: cyclopentyl-thiophosphoethanolamine, (trans-2-methylcyclopentyl)-thiophosphoethanolamine, (cis-2-methylcyclopentyl)-thiophosphoethanolamine, cyclohexyl-thiophosphoethanolamine, isopulegyl-thiophosphoethanolamine, cycloheptyl-thiophosphoethanolamine, phenyl-thiophosphoethanolamine, ortho-cresyl-thiophosphoethanolamine, (3-ethylphenyl)-thiophosphoethanolamine, (2-propylphenyl)-thiophosphoethanolamine, (3-iso-propylphenyl)-thiophosphoethanolamine, ( 2,5-dimethylphenyl)-thiophosphoethanolamine, menthyl-thiophosphoethanolamine, thymyl-thiophosphoethanolamine, carvacryl-thiophosphoethanolamine, (3-methylcyclohexyl)-thiophosphoethanolamine, and (2-ethylcyclohexyl)-thiophosphoethanolamine.

Example 29

A. This is an illustrative example of tablets containing the following ingredients which may be prepared in a conventional manner:

| Ingredients | Per Tablet (mg) |
| --- | --- |
| CPR-2006 | 50–100 |
| Lactose | 70 |
| Maize starch | 70 |
| Polyvinylpyrrolidine | 5 |
| Magnesium Stearate | 5 |
| Tablet weight | 200–250 |

B . An illustrative oil-in-water cream base formulation can be prepared for topical use from the following ingredients:

| Ingredients | Grams |
| --- | --- |
| CPR-2006 | 10.0 |
| Anhydrous lanolin | 20.0 |
| Polysorbate | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water, to | 100.0 |

C. An illustrative inhalation cartridge formulation for administration by inhalation:

| Inhalation Cartridge: | |
| --- | --- |
| Ingredients | Amount per Cartridge |
| CPR-2006, (10–50 microns) | 5.0 mg |
| Lactose q.s. | 25.0 mg |

The active ingredient, premicronized to a fine particle size 1–50 um in diameter, is blended with normal tabletting grade lactose in a high energy mixer. The powder blend is filled into appropriately sized hard gelatin capsules on a suitable encapsulation machine. The contents of the cartridges are administered using an appropriate powder inhaler.

D. An illustrative pharmaceutical composition for parenteral or intravenous administration can be prepared from the following ingredients:

| Ingredient | Amount per ampoule |
| --- | --- |
| CPR-2006 | 50 mg |
| Buffering Agent | q.s. |
| Saline | 1 mL |

E. An illustrative rectal enema formulation for administration by a suppository containing the following ingredients which may be prepared in a conventional manner:

| Ingredient | Amount per suppository |
| --- | --- |
| CPR-2006 | 500 mg |
| Hydrogenated Cocoglyceride | 5 g |

The active ingredient and pharmaceutically-acceptable vehicle are thoroughly mixed and shaped into an appropriate form.

F. An illustrative rectal enema formulation for administration by a rectal enema unit containing the following ingredients which may be prepared in a conventional manner:

| Ingredient | Amount per rectal enema unit |
| --- | --- |
| CPR-2006 | 4 g |
| Buffering Agent | q.s. |
| Saline | 60 mL |

The active ingredient and buffering agents are dissolved in the saline solution. The resultant solution is filtered and is filled into a rectal enema unit.

G. An illustrative example of capsules containing the following ingredients which may be prepared in a conventional manner:

| Ingredients | Per Capsule (mg) |
| --- | --- |
| CPR-2006 | 50 |
| Lactose | 450 |
| Magnesium Stearate | 5 |
| Capsule weight | 505 |

H. An illustrative example of water-soluble gels containing the following ingredients which may be prepared in a conventional manner:

| Ingredients | Per Packet (mg) |
|---|---|
| CPR-2006 | 195 |
| Carbomer 934P | 400 |
| Propylene glycol | 400 |
| Purified water, to | 2900 |
| Package weight | 3895 |

I. An illustrative example of water-insoluble ointments containing the following ingredients which may be prepared in a conventional manner:

| Ingredients | Per Tube (g) |
|---|---|
| CPR-2006 | 1.0 |
| Lactose | 2.0 |
| Mineral Oil | 11.0 |
| Polyethylene | 6.0 |
| Tube weight | 20.0 |

J. An illustrative example of lotions containing the following ingredients which may be prepared in a conventional manner:

| Ingredients | Per Bottle |
|---|---|
| CPR-2006 | 1.425 mg |
| Cetyl Alcohol | 2 mL |
| Steric Acid | 2 mL |
| Glycerine | 15 mL |
| Triethanolamine | 4 mL |
| Purified Water, to | 24 mL |
| Bottle volume | 57 mL |

Other compounds of Formula I, including the pharmaceutically-acceptable salts and isomers thereof, can of course be substituted for the foregoing specific compound in A–J, utilizing a relative amount of such other compounds in the composition depending on the effective activity of the particular compound.

It is understood that the invention is not limited to the compounds, compositions, methods, reagents and reactions described above, but encompasses all modifications thereof as are encompassed by the following claims.

We claim:

1. A method of treating inflammation, arrhythmia or local pain in a mammal comprising administering to such mammal an effective anti-inflammatory, anti-arrhythmic or local anesthetic amount, respectively, of a compound having the Formula I:

R—O—PEA     I wherein:

R is an unsubstituted or a substituted $C_{5-7}$ cycloalkyl of the formula:

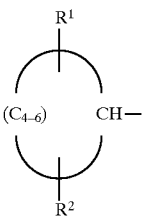

or an unsubstituted or a substituted phenyl of the formula:

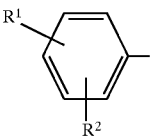

in which each $R^1$ and $R^2$ independently represents an unsubstituted or a substituted straight or branched $C_{1-4}$ alkyl or $C_{2-4}$ alkenyl, said substitution being one or more of $C_{1-4}$ alkoxy, halo or cyano; and O—PEA represents a phosphoethanolamine moiety of the formula:

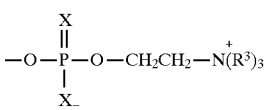

in which each $R^3$ is independently hydrogen or methyl and each X is independently oxygen or sulfur; pharmaceutically-acceptable salts thereof, and isomers thereof.

2. The method of claim 1 wherein said Formula I compounds have the formula:

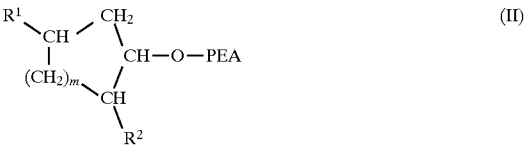

wherein m is the integer 1,2 or 3 and $R^1$, $R^2$ and O—PEA are as defined in claim 1.

3. The method of claim 1 wherein R is menthyl.

4. The method of claim 1 wherein said Formula I compounds have the formula:

wherein $R^1$, $R^2$ and O—PEA are as defined in claim 1.

5. The method of claim 1 wherein R is thymyl.

6. The method of claim 1 wherein said Formula I compound is menthylphosphocholine or thymylphosphocholine.

7. The method of claim 1 wherein said Formula I compound is selected from the group consisting of:
cyclopentylphosphoethanolamine;
thymyl-dithiophosphocholine;
thymyl-dithiophospho-(N,N-dimethylethanolamine);

(2-methylcyclohexyl)-dithiophosphoethanolamine;
(2-methylcyclohexyl)-dithiophospho-(N-methylethanolamine);
(2-methylcyclohexyl)-dithiophosphocholine; and
(2-iso-propylphenyl)-thiophosphoethanolamine.

8. A method of treating inflammation in a mammal which comprises administering to said mammal an effective anti-inflammatory amount of a compound having the Formula I:

R—O—PEA  I wherein:

R is an unsubstituted or a substituted $C_{5-7}$ cycloalkyl of the formula:

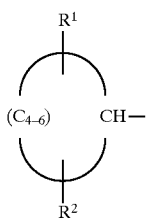

or an unsubstituted or a substituted phenyl of the formula:

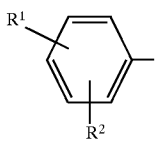

in which each $R^1$ and $R^2$ independently represents an unsubstituted or a substituted straight or branched $C_{1-4}$ alkyl or $C_{2-4}$ alkenyl, said substitution being one or more of $C_{1-4}$ alkoxy, halo or cyano; and O—PEA represents a phosphoethanolamine moiety of the formula:

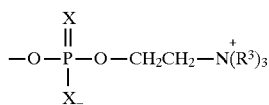

in which each $R^3$ is independently hydrogen or methyl and each X is independently oxygen or sulfur; pharmaceutically-acceptable salts thereof, and isomers thereof.

9. The method of claim 8 wherein said Formula I compounds have the formula:

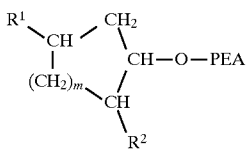

wherein m is the integer 1,2 or 3 and $R^1$, $R^2$ and O—PEA are as defined in claim 1.

10. The method of claim 8 wherein R is menthyl.

11. The method of claim 8 wherein said Formula I compounds have the formula:

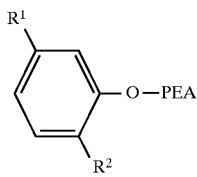

wherein $R^1$, $R^2$ and O—PEA are as defined in claim 1.

12. The method of claim 8 wherein R is thymyl.

13. The method of claim 8 wherein said Formula I compound is menthylphosphocholine or thymylphosphocholine.

14. The method of claim 8 wherein said Formula I compound is selected from the group consisting of:
cyclopentylphosphoethanolamine;
thymyl-dithiophosphocholine;
thymyl-dithiophospho-(N,N-dimethylethanolamine);
(2-methylcyclohexyl)-dithiophosphoethanolamine;
(2-methylcyclohexyl)-dithiophospho-(N-methylethanolamine);
(2-methylcyclohexyl)-dithiophosphocholine; and
(2-iso-propylphenyl)-thiophosphoethanolamine.

15. A method of treating arrhythmia in a mammal which comprises administering to said mammal an effective anti-arrhythmic amount of a compound having the Formula I:

R—O—PEA  I wherein:

R is an unsubstituted or a substituted $C_{5-7}$ cycloalkyl of the formula:

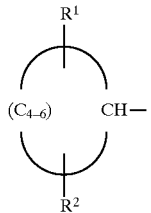

or an unsubstituted or a substituted phenyl of the formula:

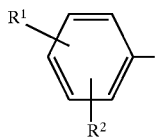

in which each $R^1$ and $R^2$ independently represents an unsubstituted or a substituted straight or branched $C_{1-4}$ alkyl or $C_{2-4}$ alkenyl, said substitution being one or more of $C_{1-4}$ alkoxy, halo or cyano; and O—PEA represents a phosphoethanolamine moiety of the formula:

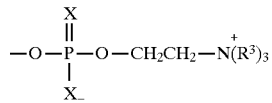

in which each $R^3$ is independently hydrogen or methyl and each X is independently oxygen or sulfur; pharmaceutically-acceptable salts thereof, and isomers thereof.

16. The method of claim 15 wherein said Formula I compounds have the formula:

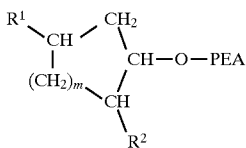 (II)

wherein m is the integer 1, 2 or 3 and $R^1$, $R^2$ and O—PEA are as defined in claim 1.

17. The method of claim 15 wherein R is menthyl.

18. The method of claim 15 wherein said Formula I compounds have the formula:

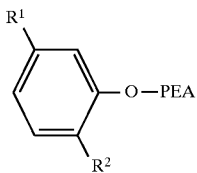 (III)

wherein $R^1$, $R^2$ and O—PEA are as defined in claim 1.

19. The method of claim 15 wherein R is thymyl.

20. The method of claim 15 wherein said Formula I compound is menthylphosphocholine or thymylphosphocholine.

21. The method of claim 15 wherein said Formula I compound is selected from the group consisting of:

cyclopentylphosphoethanolamine;
thymyl-dithiophosphocholine;
thymyl-dithiophospho-(N,N-dimethylethanolamine);
(2-methylcyclohexyl)-dithiophosphoethanolamine;
(2-methylcyclohexyl)-dithiophospho-(N-methyl-ethanolamine);
(2-methylcyclohexyl)-dithiophosphocholine; and
(2-iso-propylphenyl)-thiophosphoethanolamine.

22. A method of treating local pain in a mammal which comprises administering to said mammal an effective local anesthetic amount of a compound having the Formula I:

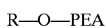 I wherein:

R is an unsubstituted or a substituted $C_{5-7}$ cycloalkyl of the formula:

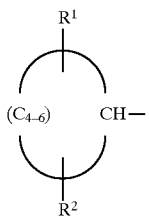

or an unsubstituted or a substituted phenyl of the formula:

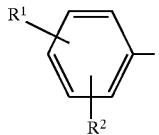

in which each $R^1$ or $R^2$ independently represents an unsubstituted or a substituted straight or branched $C_{1-4}$ alkyl or $C_{2-4}$ alkenyl, said substitution being one or more of $C_{1-4}$ alkoxy, halo or cyano; and O—PEA represents a phosphoethanolanine moiety of the formula:

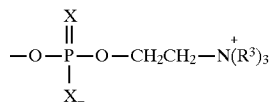

in which each $R^3$ is independently hydrogen or methyl and each X is independently oxygen or sulfur; pharmaceutically-acceptable salts thereof, and isomers thereof.

23. The method of claim 22 wherein said Formula I compounds have the formula:

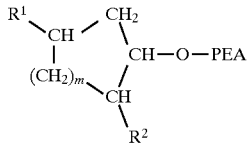 (II)

wherein m is the integer 1,2 or 3 and $R^1$, $R^2$ and O—PEA are as defined in claim 1.

24. The method of claim 22 wherein R is menthyl.

25. The method of claim 22 wherein said Formula I compounds have the formula:

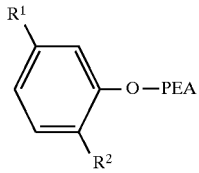 (III)

wherein $R^1$, $R^2$ and O—PEA are as defined in claim 1.

26. The method of claim 22 wherein R is thymyl.

27. The method of claim 22 wherein said Formula I compound is menthylphosphocholine or thymylphosphocholine.

28. The method of claim 22 wherein said Formula I compound is selected from the group consisting of:

cyclopentylphosphoethanolamine;
thymyl-dithiophosphocholine;
thymyl-dithiophospho-(N,N-dimethylethanolarnine);
(2-methylcyclohexyl)-dithiophosphoethanolamine;
(2-methylcyclohexyl)-dithiophospho-(N-methyl-ethanolamine);
(2-methylcyclohexyl)-dithiophosphocholine; and
(2-iso-propylphenyl)-thiophosphoethanolamine.

29. A pharmaceutical composition comprising an effective anti-inflammatory, anti-arrhythmic or local anesthetic amount of a compound of Formula I:

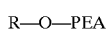 I wherein:

R is an unsubstituted or a substituted $C_{5-7}$ cycloalkyl of the formula:

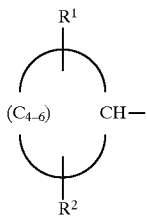

or an unsubstituted or a substituted phenyl of the formula:

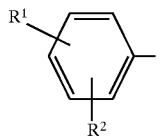

in which each $R^1$ and $R^2$ independently represents an unsubstituted or a substituted straight or branched $C_{1-4}$ alkyl or $C_{2-4}$ alkenyl, said substitution being one or more of $C_{1-4}$ alkoxy, halo or cyano; and O—PEA represents a phosphoethanolamine moiety of the formula:

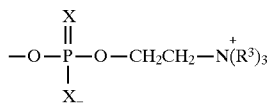

in which each $R^3$ is independently hydrogen or methyl and each X is independently oxygen or sulfur; pharmaceutically-acceptable salts thereof, and isomers thereof;

in combination with a pharmaceutically-acceptable carrier.

30. The pharmaceutical composition of claim 29 wherein said Formula I compounds have the formula:

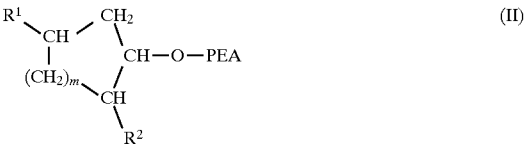

wherein m is the integer 1, 2 or 3 and $R^1$, $R^2$ and O—PEA are as defined in claim 29.

31. The pharmaceutical composition of claim 29 wherein R is menthyl.

32. The pharmaceutical composition of claim 29 wherein said Formula I compounds have the formula:

wherein $R^1$, $R^2$ and O—PEA are as defined in claim 29.

33. The pharmaceutical composition of claim 29 wherein R is thymyl.

34. The pharmaceutical composition of claim 29 wherein said Formula I compound is menthylphosphocholine or thymylphosphocholine.

35. The pharmaceutical composition of claim 29 wherein said Formula I compound is selected from the group consisting of:

cyclopentylphosphoethanolamine;
thymyl-dithiophosphocholine;
thymyl-dithiophospho-(N,N-dimethylethanolamine);
(2-methylcyclohexyl)-dithiophosphoethanolamine;
(2-methylcyclohexyl)-dithiophospho-(N-methyl-ethanolamine);
(2-methylcyclohexyl)-dithiophosphocholine; and
(2-iso-propylphenyl)-thiophosphoethanolamine.

* * * * *

UNITED STATES PATENT AND TRADEMARK OFFICE
CERTIFICATE OF CORRECTION

PATENT NO : 5,804,569
DATED : September 8, 1998
INVENTOR(S): Andrew C. Peterson and Haridasan K. Nair It is certified that error appears in the above-identified patent and that said Letters Patent is hereby corrected as shown below:

On the title sheet, please delete the title of the invention and insert therefor the correct spelling of the invention title:

--EXOCYCLIC-PHOSPHOETHANOLAMINES--.

Signed and Sealed this

Twelfth Day of January, 1999

Attest:

Attesting Officer

*Acting Commissioner of Patents and Trademarks*